(12) United States Patent
Maiti et al.

(10) Patent No.: US 7,820,409 B2
(45) Date of Patent: Oct. 26, 2010

(54) CHIMERIC HUMAN GROWTH HORMONE DERIVED FROM THE PLACENTA AND PITUITARY ISOFORM AND PROCESSES FOR OBTAINING SAID CHIMERA

(75) Inventors: Dipanwita Maiti, Mumbai (IN); Shrikant Misiira, Mumbai (IN); Laxmi Srinivas Rao, Mumbai (IN); Milind Prabhakar Nipiiadkar, Mumbai (IN); Ahmed Monsur Borbiiuiya, Mumbai (IN); Ganesh Aruna Khare, Mumbai (IN)

(73) Assignee: USV, Ltd., Mumbai (IN)

( * ) Notice: Subject to any disclaimer, the term of this patent is extended or adjusted under 35 U.S.C. 154(b) by 482 days.

(21) Appl. No.: 11/464,251

(22) PCT Filed: Jun. 23, 2004

(86) PCT No.: PCT/IN2004/000182

§ 371 (c)(1),
(2), (4) Date: Aug. 14, 2006

(87) PCT Pub. No.: WO2006/001027

PCT Pub. Date: Jan. 5, 2006

(65) Prior Publication Data

US 2007/0128622 A1    Jun. 7, 2007

(51) Int. Cl.
*C12N 15/18* (2006.01)
*C12N 15/63* (2006.01)
*C12N 1/21* (2006.01)
*C12N 5/00* (2006.01)

(52) U.S. Cl. ............ 435/69.7; 435/69.4; 435/325; 435/243; 435/252.33; 435/320.1; 536/23.4; 536/23.51

(58) Field of Classification Search ............ None
See application file for complete search history.

(56) References Cited

U.S. PATENT DOCUMENTS

| | | | |
|---|---|---|---|
| 3,853,832 A | 12/1974 | Li | |
| 4,342,832 A | 8/1982 | Goeddel et al. | |
| 4,446,235 A | 5/1984 | Seeburg | |
| 4,601,980 A | 7/1986 | Goeddel et al. | |
| 4,604,359 A | 8/1986 | Goeddel et al. | |
| 4,665,160 A | 5/1987 | Seeburg | |
| 4,670,393 A | 6/1987 | Seeburg | |
| 4,745,069 A | 5/1988 | Mayne et al. | |
| 4,755,465 A | 7/1988 | Gray et al. | |
| 4,859,600 A | 8/1989 | Gray et al. | |
| 4,859,765 A | 8/1989 | Nestor, Jr. et al. | |
| 5,047,333 A | 9/1991 | Grandi et al. | |
| 5,279,947 A | 1/1994 | Legoux et al. | |
| 5,496,713 A | 3/1996 | Honjo et al. | |
| 5,597,709 A | 1/1997 | Rosen et al. | |
| 5,618,697 A | 4/1997 | Dalboge et al. | |
| 5,633,352 A | 5/1997 | Dalboge et al. | |
| 5,635,604 A | 6/1997 | Dalboge et al. | |
| 5,688,666 A | 11/1997 | Bass et al. | |
| 5,789,199 A | 8/1998 | Joly et al. | |
| 5,849,535 A | 12/1998 | Cunningham et al. | |
| 5,955,323 A | 9/1999 | Chen et al. | |
| 5,955,346 A | 9/1999 | Wells et al. | |
| 6,436,674 B1 | 8/2002 | Honjo et al. | |
| 7,045,318 B2 * | 5/2006 | Ballance | ............ 435/69.7 |

FOREIGN PATENT DOCUMENTS

| | | |
|---|---|---|
| EP | 0489711 A2 | 6/1992 |
| EP | 0587427 A1 | 3/1994 |
| EP | 0974654 A2 | 1/2004 |
| GB | 2055382 A | 3/1981 |
| JP | 60045595 A | 3/1985 |
| JP | 61202689 A | 9/1986 |
| JP | 61224988 A | 10/1986 |
| KR | 910000458 B1 | 1/1991 |
| KR | 910000459 B1 | 1/1991 |
| WO | WO9115589 A1 | 10/1991 |

OTHER PUBLICATIONS

Accession No. CD512745 (NIH-MGC http://mgc.nci.nih.gov/, Jun. 6, 2003).*
Joseph A. Martial et al., "Human Growth Hormone: Complimentary DNA Cloning . . . ," 205 Science 602 (1979).
M.C. Lacroix et al., "Human Placental Growth Hormone—A Review," 23 Placenta (Supplement A) S87 (2002) (Elsevier Science Ltd., publ.).
Alexey A. Schulga et al., "Increased Stability of Human Growth Hormone . . . ," 528 FEBS Letters 257 (2002) (Elsevier Science B.V., publ.).
Gregory L. Gray et al., "Periplasmic Production of Correctly Processed Human Growth Hormone . . . ," 39 Gene 247 (1985) (Elsevier Science publ.).
Chen, E.Y., et al., "The Growth Hormone Locus: Nucleotide Sequence, Biology and Evolution," Genomics (1989) 4: 479-497.
Seeburg, P.H., "The Human Growth Hormone Gene Family: Nucleotide Sequence Shows Recent Divergence and Predict a New Polypeptide Hormone," DNA (1982) 1: 239-249.
Hennen, G., et al., "A Human Placental GH: Increasing Levels During Second Half of Pregnancy with Pituitary GH Suppression as Revealed by Monoclonal Antibody Assays," Intl. J. of Fertility (1985) 30: 27-33.

(Continued)

Primary Examiner—Christine J Saoud
(74) Attorney, Agent, or Firm—Pharmaceutical Patent Attorneys, LLC

(57) ABSTRACT

A way to increase the production of recombinant polypeptides by combining pieces of several different isoforms of a given gene to make a chimeric isoform of the gene (using a chimeric gene can increase the production of polypeptide over 25%), or by inserting several copies of the coding region in tandem into a transformation vector (e.g., plasmids carrying multiple copies of the chimera of SEQ ID NO: 3 increased production 107%).

8 Claims, 10 Drawing Sheets

OTHER PUBLICATIONS

Macleod, J.N., et al., "Human Growth Hormone Variant is a Biologically Active Somatogen and Lactogen," Endocrinology (1991) 128: 1298-1302.

Frankenne F., et al., " Identification of Placental Human Growth Hormone as the Growth Hormone-V Gene Expression Product," J. of Clinical Endocrinology and Metabolism (1990) 71:15-18.

Cooke, N. K., et al., "Two Distinct Species of Human Growth Hormone-Varient mRNA in the Human Placenta Predict the Expression of Novel Growth Hormone Proteins," J. of Biol. Chem. (1988) 263: 9001-9006.

Denoto, F.M., et al., "Human Growth Hormone DNA Sequence and mRNA Structure: Possible Alternative Splicing," Nucleic Acids Research (1981), 0: 3719-3730.

Untergasser, G., et al., "Complex Alternative Splicing of the GH-V Gene in the Human Testis," Eur. J. of Endocrinology (1998) 139: 424-427.

Patel, N., et al., "Glucose Inhibits Human Placental GH Secretion, in vitro," J. of Clinical Endocrinology and Metabolism (1995) 80: 1743-1746.

Lytras, A., et al., "Detection of Placental Growth Hormone Variant and chorionic Somatomammotropin Ribonucleic Acid Expression in Human Trophoblastic Neoplasm by Reverse Transcriptase-Polymerase Chain Reaction," Endocrinology (1994) 134: 2461-2467.

Henner, G., "Human Placental Growth Hormone—From Basic Research to (in vitro) Diagnostics," Global Healthcare (2002) 1-2.

Igout, A., et al., "Cloning and Nucleotide Sequence of Placental hGH-V cDNA," Arch. Int. Physiol Biochim (1988) 96: 63-67.

Wood, P., "Growth Hormone: Its Measurement and the Need for Assay Harmonization," Ann. Clin Biochem. (2001) 38:471-482.

Cunningham, B.C., et al., "Receptor and Antibody Epitopes in Human Growth Hormone Identified by Homolog-scanning Mutagenesis," Science (1989) 243: 1330-1336.

Mukhija, R., et al., "High-level Production and One-step Purification of Biologically Active Human Growth Hormone in *Escherichia coli*," Gene (1995) 165: 303-306.

Ucida, H., et al., "Secretion of Authentic 20-kDa Human Growth Hormone (20K hGH) in *Escherichia coli* and Properties of the Purified Product," J. of Biotech. (1997) 55: 101-112.

Barsh, G.S., et al., "The Human Growth Hormone Gene Family: Structure and Evolution of the Chromosome Locus," Nucleic Acids Res. (1983) 11: 3939-3958.

Lecomte, C.M., et al., "A New Natural hGH Variant 17.5 kd Produced by Alternative Splicing. An Additional Consensus Sequence, Which Might Play a Role in Branch Point Selection," Nucleic Acids Res. (1987) 15: 6331-6348.

Goeddel, D., et al., "Direct Expression in *Escherichia coli* of a DNA Sequence Coding for Human Growth Hormone," Nature (1979) 281: 544-548.

Lewis, U., "Variants of Growth Hormone and Prolactin and their Posttranslational Modifications," Ann. Rev. Physiol. (1984) 46: 33-42.

Russell, J., et al., "Recombinant Hormones form Fragments of Human Growth Hormone and Human Placental Lactogen," J. Biol. Chem. (1981) 256: 296-300.

Maxam, A.M. and Gilbert, W., "A New Method for Sequencing DNA," Proc. Natl. Acad. Sci. USA (1977) 74: 560-564.

Sononick, D. "Alternative Splicing Caused by RNA Secondary Structure," Cell (1985) 43: 667-676.

Singh, R.N.P, et al., "Heterogeneity of Human Growth Hormone," Endocrinol. Res. Commun. (1974) 1: 449-484.

Lewis, U.J., et al., "The 20,000 Dalton Variant of Human Growth Hormone: Location of the Amino Acid Deletions," Biochem. Biophys. Res. Commun. (1980) 92: 511-516.

Hirt, H., et al., "The Human Growth Hormone Gene Locus: Structure, Evolution and Allelic Variations," DNA (1987) 6:59-70.

Parks, J.S., et al., "Evolution and Structure of the Growth Hormone Gene Cluster. In 'Advances in Growth Hormone and Growth Factor Research'," Ed. E. Meuller. Springer-Verlag (1989) 3-17.

Fiddes, J., et al., "Structure of Genes For Human Growth Hormone and Chorionic Somatomammotropin," Proc. Natl. Acad. Sci. USA 76: 4294-4298.

Selby, M.J., et al., "Analysis of a Major Human Chorionic Somatomammotropin Gene. Evidence for Two Functional Promoter Elements," J. of Biol. Chem. (1984) 259: 13131-13138.

Tanaka, T., et al., "A New Sensitive and Specific Bioassay for Lactogenic Hormones, Measurement of Prolactin and Growth Hormone in Human Serum," Clin. Endocrinol. Metab. (1980) 51: 1058-1063.

Ealey, P.A., et al., "The Development of an Eluted Stain Bioassay (ESTA) for Human Growth Hormone," Growth Regulation (1995) 5: 36-44.

Yanisch-Perron, C., et al., "Improved M13 Phage Cloning Vectors and Host Strains: Nucleotide Sequences of the M13mp18 and pUC19 Vectors," Gene (1985) 33: 103-119.

Sambrook, J., Fritsch, E.F., and Maniatis, T., "Molecular Cloning: A Laboratory Manual (2nd Edition)" (1989) 1-1659.

Kraft, R., et al., "Using Mini-prep Plasmid DNA for Sequencing Double Stranded Templates with Sequenase," BioTechniques (1988) 6: 544-547.

Ausubel, F.M., et al., "Current Protocols in Molecular Biology," (1997) John Wiley & Sons, Inc., vol. 3.

Igout, A., et al., "Purification of Biochemical Characterization of Recombinant Human Placental Growth Hormone Produced in *Escherichia coli*," Biochem. J. (1993) 295: 719-724.

Shin, N-K., et al., "High-level Production of Human Growth Hormone in *Escherichia coli* by a Simple Recombinant Process," J. of Biotechnol (1998) 62: 143-151.

Chang, C.N., et al., "High-level Secretion of Human Growth Hormone by *Escherichia coli*," Gene (1987) 55: 189-196.

Hsiung, H.M., et al., "High-level Expression, Efficient Secretion and folding of Human Growth Hormone in *Escherichia coli*," Biotechnology (1986) 4: 991-995.

Tokunaga, T., et al., "Synthesis and Expression of a Human Growth Hormone (somatotropin) Gene Mutated to Change Cysteine-165 to Alanine," Eur. J. Biochem (1985) 153: 445-449.

* cited by examiner

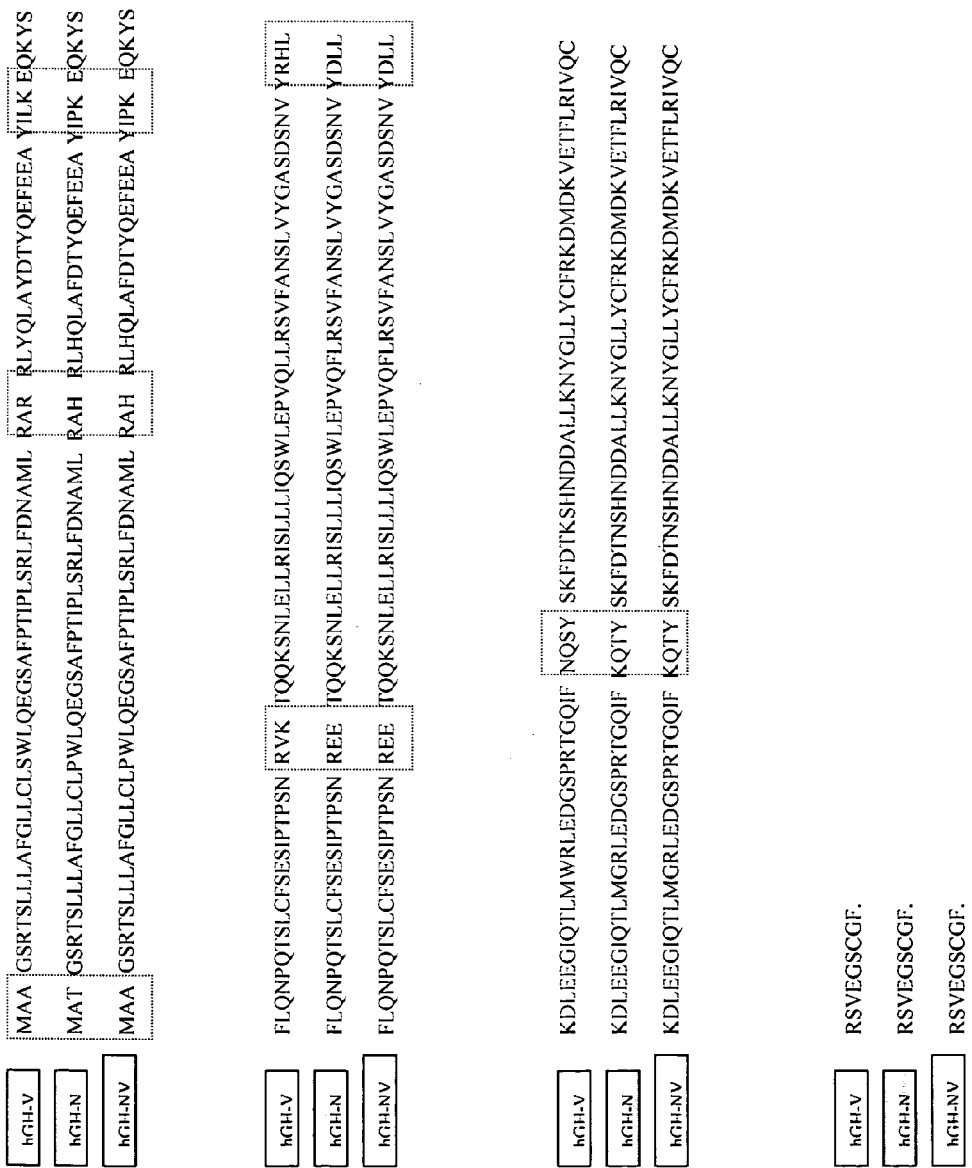
Figure 2. Comparison of Human Growth Hormone Protein Sequences

A. RNA Folding of hGH-N ORF. Seq.

B. RNA Folding of hGH-NV ORF. Seq.

The Min. Energy of both (hGH-N ORF, SEQ ID NO:2 and hGH-NV ORF, SEQ ID NO:3) although is comparable, they greatly differ in their RNA secondary structure due to their sequence difference.

Bioactivity Assay of hGH-NV derived hGH

A.  Coomassie Stained Gel

Here, pABGH1' refers Pituitary cDNA derived hGH (Chen et al., 1989, lane 5 & 6) clone, pABGH1 (lane 7 & 8) refers chimeric hGH-NV derived synthetic hGH clone and pABGH2 (lane 3 & 4) refers the later insert in duplicates.

B. Percentage of hGH expression is shown below using Densitometric scan

| Clone # | % of hGH Expression |
|---------|---------------------|
| pABGH2  | 11.2                |
| pABGH1' | 4.3                 |
| pABGH1  | 5.4                 |

```
                         SEQUENCE LISTING

<160> NUMBER OF SEQ ID NOS: 22

<210> SEQ ID NO 1
<211> LENGTH: 694
<212> TYPE: DNA
<213> ORGANISM: Homo sapiens

<400> SEQUENCE: 1
ctgtggacag ctcaggtacc ggcaatggct gcaggctccc ggacgtccct gctcctggct     60
tttggcctgc tctgcctgtc ctggcttcaa gagggcagtg ccttcccaac cattcccttc    120
tccaggcttt ttgacaacgc tatgctccgc gcccgtcgcc tgtaccagct ggcatatgac    180
acctatcagg agtttgaaga agcctatatc ctgaaggagc agaagtattc attcctgcag    240 aaccccagc cctccctctg cttctcagag tctattccaa caccttccaa cagggtgaaa     300
acgcagcaga aatctaacct agagctgctc cgcatctccc tgctgctcat ccagtcatgg    360
ctggagcccg tgcagctcct caggagcgtc ttcgccaaca gcctggtgta tggcgcctcg    420
gacagcaacg tctatcgcca cctgaaggac ctagaggaag catccaaac gctgatgtgg    480 aggctggaag atggcagccc ccggactggg cagatcttca atcagtccta cagcaagttt    540
gacacaaaat cgcacaacga tgacgcactg ctcaagaact acgggctgct ctactgcttc    600
aggaaggaca tggacaaggt cgagacattc ctgcgcatcg tgcagtgccg ctctgtggag    660
ggcagctgtg gcttctagct gcacggatcc catc                               694

<210> SEQ ID NO 2
<211> LENGTH: 723
<212> TYPE: DNA
<213> ORGANISM: Homo sapiens

<400> SEQUENCE: 2
ccaaggccca actccccgaa ccactcaggg tcctgtggac agctcaccta gcggcaatgg     60
ctacaggctc ccggacgtcc ctgctcctgg cttttggcct gctctgcctg cctggcttc    120 aagagggcag tgccttccca accattccct tatccaggct ttttgacaac gctatgctcc    180
gcgcccatcg tctgcaccag ctggcctttg acacctacca ggagtttgaa gaagcctata    240
tcccaaagga acagaagtat tcattcctgc agaaccccca gacctccctc tgtttctcag    300
agtctattcc gacaccctcc aacagggagg aaacacaaca gaaatccaac ctagagctgc    360
```

```
tccgcatctc cctgctgctc atccagtcgt ggctggagcc cgtgcagttc ctcaggagtg      420
tcttcgccaa cagcctggtg tacggcgcct ctgacagcaa cgtctatgac ctcctaaagg      480
acctagagga aggcatccaa acgctgatgg ggaggctgga agatggcagc ccccggactg      540
ggcagatctt caagcagacc tacagcaagt tcgacacaaa ctcacacaac gatgacgcac      600
tactcaagaa ctacgggctg ctctactgct tcaggaagga catggacaag gtcgagacat      660
tcctgcgcat cgtgcagtgc cgctctgtgg agggcagctg tggcttctag ctgcccgggt      720
ggc                                                                    723

<210> SEQ ID NO 3
<211> LENGTH: 728
<212> TYPE: DNA
<213> ORGANISM: Artificial
<220> FEATURE:
<223> OTHER INFORMATION: Synthetic Primer

<400> SEQUENCE: 3
gccatggccg cgggattctg tggacagctc aggtaccgca atggctgcag gctcccggac       60
gtccctgctc ctggcttttg gcctgctctg cctgccctgg cttcaagagg gcagtgcctt      120
cccaaccatt cccttatcca ggcttttga caacgctatg ctccgcgccc atcgtctgca      180
ccagctggcc tttgacacct accaggagtt tgaagaagcc tatatcccaa aggaacagaa      240
gtattcattc ctgcagaacc cccagacctc cctctgtttc tcagagtcta ttccgacacc      300
ctccaacagg gaggaaacac aacagaaatc caacctagag ctgctccgca tctccctgct      360
gctcatccag tcgtggctgg agcccgtgca gttcctcagg agtgtcttcg ccaacagcct      420
ggtgtacggc gcctctgaca gcaacgtcta tgacctccta aaggacctag aggaaggcat      480
ccaaacgctg atggggaggc tggaagatgg cagcccccgg actgggcaga tcttcaagca      540
gacctacagc aagttcgaca caaactcaca caacgatgac gcactactca agaactacgg      600
gctgctctac tgcttcagga aggacatgga caaggtcgag acattcctgc gcatcgtgca      660
gtgccgctct gtggagggca gctgtggctt ctagctgcac ggatcccatc aatcactagt      720
gcggccgc                                                              728

<210> SEQ ID NO 4
<211> LENGTH: 591
<212> TYPE: DNA
<213> ORGANISM: Artificial
<220> FEATURE:
<223> OTHER INFORMATION: Synthetic Primer

<400> SEQUENCE: 4
tcccaaccat tcccttatcc aggcttttg acaacgctat gctccgcgcc catcgtctgc       60
accagctggc ctttgacacc taccaggagt ttgaagaagc ctatatccca aaggaacaga      120
agtattcatt cctgcagaac ccccagacct ccctctgttt ctcagagtct attccgacac      180
cctccaacag ggaggaaaca acagaaatc caacctaga gctgctccgc atctccctgc      240
tgctcatcca gtcgtggctg agcccgtgc agttcctcag gagtgtcttc gccaacagcc      300
tggtgtacgg cgcctctgac agcaacgtct atgacctcct aaaggaccta gaggaaggca      360
tccaaacgct gatggggagg ctggaagatg gcagcccccg gactgggcag atcttcaagc      420
agacctacag caagttcgac acaaactcac acaacgatga cgcactactc aagaactacg      480
ggctgctcta ctgcttcagg aaggacatgg acaaggtcga cattcctg cgcatcgtgc      540
```

-continued agtgccgctc tgtggagggc agctgtggct tctagtaact cgagtggccg c    591

<210> SEQ ID NO 5
<211> LENGTH: 579
<212> TYPE: DNA
<213> ORGANISM: Artificial
<220> FEATURE:
<223> OTHER INFORMATION: Chimeric sequence

<400> SEQUENCE: 5
ttcccaacca ttcccttatc caggcttttt gacaacgcta tgctccgcgc ccatcgtctg    60
caccagctgg cctttgacac ctaccaggag tttgaagaag cctatatccc aaaggaacag    120
aagtattcat tcctgcagaa cccccagacc tccctctgtt tctcagagtc tattccgaca    180
ccctccaaca gggaggaaac acaacagaaa tccaacctag agctgctccg catctccctg    240
ctgctcatcc agtcgtggct ggagcccgtg cagttcctca ggagtgtctt cgccaacagc    300
ctggtgtacg gcgcctctga cagcaacgtc tatgacctcc taaaggacct agaggaaggc    360
atccaaacgc tgatggggag gctggaagat ggcagccccc ggactgggca gatcttcaag    420
cagacctaca gcaagttcga cacaaactca cacaacgatg acgcactact caagaactac    480
gggctgctct actgcttcag gaaggacatg gacaaggtcg agacattcct gcgcatcgtg    540
cagtgccgct ctgtggaggg cagctgtggc ttctagtaa    579

<210> SEQ ID NO 6
<211> LENGTH: 29
<212> TYPE: DNA
<213> ORGANISM: Artificial
<220> FEATURE:
<223> OTHER INFORMATION: Synthetic sequence

<400> SEQUENCE: 6
cctgtggaca gctcacctag cggcaatgg    29

<210> SEQ ID NO 7
<211> LENGTH: 29
<212> TYPE: DNA
<213> ORGANISM: Artificial
<220> FEATURE:
<223> OTHER INFORMATION: Synthetic Primer

<400> SEQUENCE: 7
gatgggatcc gagcagctag aagccacag    29

<210> SEQ ID NO 8
<211> LENGTH: 29
<212> TYPE: DNA
<213> ORGANISM: Artificial
<220> FEATURE:
<223> OTHER INFORMATION: Synthetic

<400> SEQUENCE: 8
ccaaggccca actccccgaa ccactcagg    29

<210> SEQ ID NO 9
<211> LENGTH: 27
<212> TYPE: DNA
<213> ORGANISM: Artificial
<220> FEATURE:
<223> OTHER INFORMATION: synthetic

<400> SEQUENCE: 9
gccacccggg cagctagaag ccacagc    27

<210> SEQ ID NO 10
<211> LENGTH: 217
<212> TYPE: PRT
<213> ORGANISM: Artificial sequence
<220> FEATURE:
<223> OTHER INFORMATION: synthetic

<400> SEQUENCE: 10

```
Met Ala Ala Gly Ser Arg Thr Ser Leu Leu Leu Ala Phe Gly Leu Leu
1               5                   10                  15

Cys Leu Ser Trp Leu Gln Glu Gly Ser Ala Phe Pro Thr Ile Pro Leu
            20                  25                  30

Ser Arg Leu Phe Asp Asn Ala Met Leu Arg Ala Arg Arg Leu Tyr Gln
        35                  40                  45

Leu Ala Tyr Asp Thr Tyr Gln Glu Phe Glu Glu Ala Tyr Ile Leu Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Val Lys Thr Gln Gln Lys
                85                  90                  95

Ser Asn Leu Glu Leu Leu Arg Ile Ser Leu Leu Ile Gln Ser Trp
            100                 105                 110

Leu Glu Pro Val Gln Leu Leu Arg Ser Val Phe Ala Asn Ser Leu Val
        115                 120                 125

Tyr Gly Ala Ser Asp Ser Asn Val Tyr Arg His Leu Lys Asp Leu Glu
    130                 135                 140

Glu Gly Ile Gln Thr Leu Met Trp Arg Leu Glu Asp Gly Ser Pro Arg
145                 150                 155                 160

Thr Gly Gln Ile Phe Asn Gln Ser Tyr Ser Lys Phe Asp Thr Lys Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215
```

<210> SEQ ID NO 11
<211> LENGTH: 217
<212> TYPE: PRT
<213> ORGANISM: Artificial sequence
<220> FEATURE:
<223> OTHER INFORMATION: Synthetic

<400> SEQUENCE: 11

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
```

```
            85                  90                  95
Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
            115                 120                 125

Tyr Gly Ala Ser Asp Ser Asn Val Tyr Asp Leu Leu Lys Asp Leu Glu
            130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
            195                 200                 205

Arg Ser Val Glu Gly Ser Cys Gly Phe
    210                 215

<210> SEQ ID NO 12
<211> LENGTH: 24
<212> TYPE: DNA
<213> ORGANISM: Artificial Sequence
<220> FEATURE:
<223> OTHER INFORMATION: Synthetic

<400> SEQUENCE: 12
tcccaaccat tcccttatcc aggc                                           24

<210> SEQ ID NO 13
<211> LENGTH: 30
<212> TYPE: DNA
<213> ORGANISM: Artificial Sequence
<220> FEATURE:
<223> OTHER INFORMATION: Synthetic

<400> SEQUENCE: 13
gcggccactc gagttactag aagccacagc                                     30

<210> SEQ ID NO 14
<211> LENGTH: 217
<212> TYPE: PRT
<213> ORGANISM: Artificial Sequence
<220> FEATURE:
<223> OTHER INFORMATION: Synthetic Primer

<400> SEQUENCE: 14

Met Ala Ala Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
            85                  90                  95

Ser Asn Leu Glu Leu Leu Arg Ile Ser Leu Leu Leu Ile Gln Ser Trp
```

```
                    100                 105                 110
Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215

<210> SEQ ID NO 15
<211> LENGTH: 17
<212> TYPE: DNA
<213> ORGANISM: Artificial Sequence
<220> FEATURE:
<223> OTHER INFORMATION: Synthetic Primer

<400> SEQUENCE: 15
gctcttctcg ctaacca                                              17

<210> SEQ ID NO 16
<211> LENGTH: 18
<212> TYPE: DNA
<213> ORGANISM: Artificial Sequence
<220> FEATURE:
<223> OTHER INFORMATION: Synthetic Primer

<400> SEQUENCE: 16
cttatcgtca tcgtcgta                                             18

<210> SEQ ID NO 17
<211> LENGTH: 31
<212> TYPE: DNA
<213> ORGANISM: Artificial Sequence
<220> FEATURE:
<223> OTHER INFORMATION: Synthetic Primer

<400> SEQUENCE: 17
gagtatgccg gcagcagggg atcattttgc g                              31

<210> SEQ ID NO 18
<211> LENGTH: 31
<212> TYPE: DNA
<213> ORGANISM: Artificial Sequence
<220> FEATURE:
<223> OTHER INFORMATION: Synthetic Primer

<400> SEQUENCE: 18
ccccaacgga atttgtcgtc gtcgtcgtcg a                              31

<210> SEQ ID NO 19
<211> LENGTH: 31
<212> TYPE: DNA
<213> ORGANISM: Artificial Sequence
<220> FEATURE:
<223> OTHER INFORMATION: Synthetic Primer
```

-continued

```
<400> SEQUENCE: 19
gatctgtacg acgatgaaat tcccaaccat t                              31

<210> SEQ ID NO 20
<211> LENGTH: 27
<212> TYPE: DNA
<213> ORGANISM: Artificial Sequence
<220> FEATURE:
<223> OTHER INFORMATION: Synthetic Primer

<400> SEQUENCE: 20
ggcactgtac aatgcgcagg aatgtct                                   27

<210> SEQ ID NO 21
<211> LENGTH: 30
<212> TYPE: DNA
<213> ORGANISM: Artificial Sequence
<220> FEATURE:
<223> OTHER INFORMATION: Synthetic Primer

<400> SEQUENCE: 21
cctgcgcatt gtacagtgcc gctctgtgga                                30

<210> SEQ ID NO 22
<211> LENGTH: 32
<212> TYPE: DNA
<213> ORGANISM: Artificial Sequence
<220> FEATURE:
<223> OTHER INFORMATION: Synthetic Primer

<400> SEQUENCE: 22
ttcagatcgg ctcccggcgg atttgtccta ct                             32
```

CHIMERIC HUMAN GROWTH HORMONE DERIVED FROM THE PLACENTA AND PITUITARY ISOFORM AND PROCESSES FOR OBTAINING SAID CHIMERA

RELATED APPLICATIONS

This application is the U.S.A. National Stage application of PCT application Serial No. PCT/IN2004/000182, the contents of which are here incorporated by reference.

GOVERNMENT INTEREST

None.

BACKGROUND

The present invention primarily relates to a novel hGH-NV cDNA chimera as shown in SEQ ID NO: 3 encoding human growth hormone (hGH) and a process for the preparation of the said novel chimera. Further the invention relates to the use of hGH-NV cDNA chimera to obtain an expressible construct to produce mature human growth hormone.

DNA Isoform and Gene Cluster

The mammalian genomic locus for growth hormone (GH, somatotropin) has expanded very recently in evolution (possibly 10 million years ago) into a cluster of five highly sequence-conserved genes (as in simians and humans). Whereas, in rodents and ungulates, the homologous locus contains solely the gene for the respective somatotropin, in humans, this locus harbors an additional four genes (Fiddes et al, 1979; Seeburg, 1982). The structure of the human growth hormone gene cluster has been determined over 78 kb region of DNA. The entire gene cluster is located on the long arm of human chromosome 17 at bands q22-q24 (George et al., 1981). The DNA sequence of 66,495 bp (contains the sequences of five genes, each consisting of five exons and four introns) reported here represents approximately 0.1% of the entire human chromosome 17. It was isolated on two overlapping recombinant cosmids (Barsh et al., 1983) and has been characterized by restriction analysis as well as with respect to the positions and transcriptional orientations.

There are two growth hormone genes interspersed with three chorionic somatomammotropin genes, all in the same transcriptional orientation. These genes cluster (5' to 3': hGH-N, hCS-L, hCS-A, hGH-V, hCS-B) of growth hormone superfamily show the same transcriptional direction and are separated by intergenic regions of 6 to 13 kb in length which contain 48 interspersed middle repetitive sequence elements of the Alu type (Chen et al., 1989, Seeburg, 1982). Among these three of them are truncated depicts the gene cluster map of the Growth hormone superfamily in tandem, which shows genes (5' to 3': hGH-N, hCS-L, hCS-A, hGH-V, hCS-B) aligned in the same transcriptional orientation and are separated by intergenic regions of 6 to 13 kb in length, which contain 48 interspersed middle repetitive sequence elements. The genes for hGH and hCS are clustered together at band q22-q24 on chromosome 17, but the prolactin gene is located on chromosome 6. All five genes, including their immediate flanking regions, have been sequenced and are conserved throughout (91-99%).

The human chromosomal growth hormone locus spans approximately 66.5 kb and was sequenced in its entirety to provide a framework for the analysis of its biology and evolution (Chen, et al., 1989; Seeburg, et al., 1982; Lewis et al., 1980; Hirt et al., 1987). hGH-N gene is transcribed exclusively in the pituitary, whereas the other four genes (hCS-L, hCS-A, hGH-V, hCS-B) are expressed only in placental tissue, at levels characteristic for each gene (Hennen, et al., 1985; Macleod, et al., 1991; Frankenne, et al., 1990). The extensive structural information allows a reconstruction of the major steps in the molecular evolution of the hGH locus, from a single ancestral growth hormone-like progenitor gene to the present five-gene arrangement on chromosome 17.

Differential Isoform Expression

Analysis of the sequences of the genes and identification of at least three different classes of duplication units interspersed throughout the five gene cluster suggests that the cluster evolved quite recently and that the mechanism of gene duplication involved homologous but unequal exchange between middle repetitive elements of the Alu family.

These groups of genes are highly homologous throughout their 5' flanking and coding sequences, but diverge in their 3' flanking regions which raises the paradox of how genes so similar in structural and flanking sequences can be so differentially regulated. Despite the high sequence identity, these genes are expressed selectively in two different tissues under differential hormonal control (Parks et al., 1989). The hGH-N gene lies in an active chromatin conformation in the pituitary, which is transcribed only in somatotrophic cells of the anterior pituitary, whereas at least one of the chorionic somatomammotropin genes lies in the placental trophoblasts.

The first step in the RNA splicing process is the selection of the 3' splice site and its polypyrimidine tract, accompanied by the association of factor(s) with an intronic branch point site is mainly determined by its distance to the 3' splice junction. Thus it seems obvious that the choice of the splice site is a key element both in the general mechanism of splicing and in the special case of alternative processing. This is in agreement with the observation that alternative RNA processing more often involves the use of an alternative acceptor site (as it occurs with hGH mRNA) than of an alternative donor site. The cell type dependent splice variant and it's stability defines the locus of the transcript.

GH/PL gene transcription is controlled in an organ-specific manner during human ontogenesis: GH-V, PL-A, PL-B and PL-L genes are transcriptionally active in the placenta (Seeburg et al, 1982), whereas after birth pituitary-derived hGH-N becomes the predominant endocrine-active GH (Selby et al., 1984). In contrast to hGH-N, placental hGH-V is synthesized during the first months of human life during pregnancy in the syncytiotrophoblast, but its functions for growth, development and metabolism are not clear (Hennen et al., 1985; Cooke et al., 1988). Among the gestational polypeptide hormones, hGH-V and placental lactogen secreted by the placenta, only hGH-V secretion is modulated by glucose, suggesting a metabolic key role for this hormone during pregnancy (Seeburg, 1982; Patel et al., 1995). The majority of total placental GH/PL mRNAs is derived from the PL-A and PL-B genes (95-99%) and only 1-4.2% encode GH-V gene products (Chen et al., 1989; MacLeod et al., 1991; Lytras et al., 1994).

Two alternatively processed mRNAs, omitting or including intron D of the GH-V gene (Untergasser, G. et al., 1998), are expressed by the syncytiotrophoblast resulting in either secreted (22K, 191 aa) or presumably membrane-associated (26K, 230 aa) proteins (Cooke et al., 1988). Secreted hGH-V alternatively termed placental hGH, a somatagen, is detectable in the serum of pregnant woman and becomes the predominant serum hGH by the third trimester of gestation (Hennen et al., 1985; Cooke et al., 1988). This information has helped us to take a novel cDNA walk from one isoform (hGH-V) to the other (hGH-N). cDNA sequence similarity and the restriction enzyme map pattern between the two were taken as the platform for this novel invention.

Both the pituitary- and placental-derived growth hormones are produced in the form of processed mature GH protein with or without any secretion signaling sequence, which is accumulated in the periplasmic or in the soluble fractions of *E. coli*, respectively (Hsiung et al., 1986; Chang et al., 1987; Martial et al., 1979; Gray et al., 1988 and Joly et al., 1998). hGH-V cDNA encodes a molecular weight of 20,000 Dalton protein (Ucida et al., 1997; Honjo et al., 1996; Igout et al., 1988 and 1993; Frankenne et al., 1990) whereas, the growth hormone is made up of 191 amino acids and has a molecular weight of 21,500 Dalton and is used for treatment of pituitary dwarfism, pediatric chronic renal failure (Mukhija et al., 1995; Grandi, 1991). hGH has recently been found to have remarkable activities such as immune promoting activity or lipolysis stimulating activity, as well as growth promoting activity. Broader applications are greatly expected in the future.

Alternative splicing of the primary hGH-N gene transcription product generates two mRNA species that respectively (DeNoto et al., 1981) encode the hGH (22 ID form) and a somatotropin variant (20 kD form), which has 15 codons deleted from exon III of hGH-N gene transcript (Singh et al., 1974; Lewis et al., 1978). No such alternative splicing is reported for the hCS gene RNAs. Perfect codon colinearity exists for all the mRNAs, with the exception of the hCS-L gene mRNA which carries a different exon III structure.

All five mRNAs specify polypeptides of approximately 200 amino acids in length, of which the N-terminal 26 residues function as signal sequences. The hGH-V gene, which is positioned between the hCS-A and -B genes, encodes a polypeptide differing from GH in 13 positions compared to hGH-N (Seeburg, 1982), while hGH differs from hCS in 28 residues The hCS-L DNA sequence revealed a point mutation in the 5' consensus splice donor site of its second intron (Hirt et al., 1987), suggesting that splicing might not occur at this position. Thus, the hCS-L gene may not yield a stable RNA or protein product. The hypothetical hCS-L protein is shorter by 18 amino acid residues than the closely related hCS and contains a stretch of 6 residues with no homology to other polypeptides, only 75% sequence identity with hGH. Spatial distribution of transcript of these five genes might be regulated at the level of transcription, or based on both position as reflected in the chromatin structure of the hGH locus, and sequence-specific regulatory elements around the individual genes could be responsible for the observed tissue-specific patterns of gene expression.

Eukaryotic Codon Usage vs. Differentiation

The DNA of genes comprises of several structurally secluded regions i.e., for regulatory as well as the full-length protein encoding open reading frame. The enzyme "RNA polymerases" becomes activated, binds in the control region (called 'promoter'), slides along the structural gene and transcribes the encoded information with the help of several other functional accessories, into a rough draft of spliced pre-messenger ribonucleic acid (pre-mRNA) and then into its finally processed messenger ribonucleic acid (mRNA). This mRNA message is then translated at the ribosomes in the form of triplet codes for each translatable amino acid, where the translation of a protein begins with the start signal (most commonly ATG) and proceeds until the stop signal (commonly TAA, TAG, TGA).

As mentioned above, the genetic code within DNA is defined by amino acids, which is specified by a triplet, or "codon" (three adjacent nucleotides from A, T, G, C) where the third nucleotide for each specific amino acid in any protein can be varied. In accordance with the genetic code preference of using the third amino acid for a specific amino acid varies among prokaryotes and eukaryotes, which defines the 'degeneracy' of codon usage among various organisms (Table 1). Percentage of codon usage and frequency of their occurrence has been clearly shown in Ausubel, F. M. et. al. (1987). Here, we have shown the variability in usage of amino acids and their frequency of occurrence among organisms in table 1 (Ausubel, F. M. et al., 1987). This knowledge tremendously helps in expression of a protein of interest in a heterologous system in recombinant technology, where nucleotides can be changed within the triplets at the DNA level to improve the yield of any foreign protein expression. Our analysis of chimeric hGH identification of those regions of the sequence that could possibly result in poor heterologous expression. We take advantage of differences in hGH-N sequence and its alleles codon usage to come up with a expression clone which can be of great help in expressing human growth hormone in various organisms like *E. coli*, yeast, insect, CHO, etc. by modifying with appropriate codon usage.

The complete sequence of the human growth hormone (hGH) gene and the position of the mature 5' end of the hGH mRNA within the sequence has been determined by DeNoto F. M. et al., 1981. Comparison of this sequence with that of a cloned hGH cDNA shows that the gene is interrupted by four intervening sequences. S1 mapping shows that one of these intervening sequences has two different 3' splice sites. These alternate splicing pathways generate hGH peptides of different sizes, which are found in normal pituitaries. Comparison of sequences near the 5' end of the hGH mRNA with a similar region of the alpha subunit of the human glycoprotein hormones reveals an unexpected region of homology between these otherwise unrelated peptide hormones.

Mechanisms of alternative RNA splicing are commonly implicated in the generation of protein diversity. Splicing at one alternative 3' site located 45 bp downstream from the normal 3' site of intervening sequence B is likely to generate the mRNA for one smaller hGH peptide found at low levels in normal pituitaries. The position of the 5' end of the mature mRNA was located using S1 mapping. S1 nuclease analysis provides evidence for the existence of multiple RNAs. hGH gene may be a good system to approach some unsolved questions about the accuracy of RNA splicing and the regulation of splice site selection in alternative pathways. The signal sequence TATAAA, thought to be involved in initiation of transcription, is found approximately 25 bp upstream from the 5' end of the mature mRNA. Conserved sequences are also found in the gene near the sequence where poly A is added to the mRNA. Surprisingly, there is a region of homology in the 5' untranslated regions of the mRNA's of hGH and the otherwise unrelated alpha-subunit of the human glycoprotein hormone. Our work; further aims in bringing the suttle differences in mRNA secondary structure of chimeric hGH for better expression. Sononick (1985) has proposed that influence of the RNA secondary structure exists on the splice sites selection. He has shown that frequently used splice sites become optional when sequestered in a hairpin loop. According to their observation there is a local secondary structure in the regions of the alternative splicing site of the hGH precursor mRNA, a large hairpin structure trapping both the 22K and the 20K acceptor sites, and also the branch point sequence of the splice site. The stable structure, by looping out the 22K and 20K splice sites and by interfering with the lariat formation leading to the specific splice site, would favour the jump splice at the alternative acceptor site.

In many introns, the computer searches have shown a well-conserved region between coordinates −60 and −21 from the 3' splicing cleavage site. This box has an additional element affecting acceptor splice site recognition and lariat formation (Leocomte et al., 1987). S1 mapping analysis of human pituitary RNA confirms the existence of at least four distinct hGH mRAs originating from alternative acceptor sites at the second intron of the primary transcript. Analysis was done on the hGH gene sequence to explain the high frequency of alternative splicing which occur only at this location. Out of the four introns of the hGH gene, three contain a "CTTG" box in the region upstream from the acceptor splice site (intron A, B, and D). However, the "CTTG" box was not found in intron C and upstream from the 20K alternative splice sites. For many introns, it has been reported that a good complementarities between the region containing the "CTTG" box and the 5'-end of the first loop of U2 snRNA might play a role in branch point selection of specifying splice sites by RNA-RNA base pairing. Generation of protein diversity in hGH possibly implicates that it is due to their differences in RNA secondary structure as well as codon usage have different levels of expression in a preferred host.

Construction of Chimera and Industrial Rationale

The construction of recombinant vector to be used in cloning comprises the construction of hybrid plasmids containing the nucleotide sequence which codes for mature protein of interest e.g., mature hGH, fused at its 5' terminal to a sequence which codes for a fusion tag peptide sequence and a protease cleavage site. The hybrid plasmid thus are made heterologous by making chimeric DNA construct which has made its potential application in lab scale as well as in large scale in recent years. Concept of construction of chimera with the gene of interest in recombinant technology facilitates yield of expression as well as the purification steps. Success rates in both aspects depend on the choice of the fusion peptide selected.

Immobilized metal ion affinity chromatography (IMAC) is most widely used technique for purification of recombinant proteins. Engineering of His-tag on the amino or carboxyl terminal of protein allows selective absorption of the recombinant protein on immobilized metal ions, such as $Ni^{2+}$, $Co^{2+}$, $Zn^{2+}$, $Cu^{2+}$, and $Fe^{2+}$. These techniques provide selective purification of the target protein (Mukhija et al 1995; Shin et al., 1998; WO 9115589). Use of basic amino residues comprising of Histidine or Lysine or Arginine allows the invention to be worked effectively.

Overall the selection and application in making the chimeric construct aids the percentage of product yield in pilot scale as well as in large scale in an industrial background. Keeping a protease cleavage site (e.g., thrombin, factor V, factor Xa, serine proteases site like enterokinase) right after the affinity tag (either His-tag or GST-tag) is commonly used in the chimera construction where expressed heterologous protein is easily cleaved off from the tag either on the column or outside the column and the protein of interest having the sequence of naturally occurring hGH, is isolated. Choice of the affinity chromatographic technique helps in handling any large batch purification for industrial purpose with fewer steps in purification and reduces the loss of the final product of interest, thus making the whole process cost effective.

History of Cloning of hGH

Human growth hormone (hGH) is secreted in the human pituitary. In its mature form it consists of 191 amino acids, has a molecular weight of about 21,500 and thus is more than three times as large as insulin. Until the advent of recombinant DNA technology, hGH could be obtained only be laborious extraction from a limited source i.e., the pituitary, glands of human cadavers. The consequent scarcity of the substance has limited its application to treatment of hypopituitary dwarfism even though it has been proposed to be effective in the treatment of burns, wound healing, dystrophy, bone knitting, diffuse gastric bleeding and pseudarthrosis. In fact, available estimates are that the amount of hGH available from tissue is adequate only to serve about 50% of the victims of hypopituitary dwarfism. Thus, no hGF is available for other applications. Hence, it is required to take the advantage of recombinant DNA technology for cloning of hGH and production specifically in E. coli. The use of E. coli as a microbial host for complex heterologous polypeptides is now well-established in micorbial host. First it has been shown that hGH can be produced in a recombinant host cell, specifically E. coli in good quantities which would be adequate to treat hypopituitary dwarfism and the other conditions for which it is effective (for example, U.S. Pat. No. 4,342,832). hGH expressed by the process of U.S. Pat. No. 4,342,832 leads to a product, which can be used for therapeutic applications. Later, various modifications were done generating vector constructs for hGH expression in E. coli (also in Bacillus and Pseudomonas). So far, E. coli generated recombinant hGH has been well accepted by the patient as it does not give any immunogenic reaction. Since this is not a glycoprotein, E. coli is the most suitable host for expressing hGH.

Attempts have been made in making vector constructs with specific regulatory elements to control the site of expression & yield of expression in E. coli host system as well as at the level of expressed proteins secondary structure formation during cloning steps (Tokunaga et al., 1985). There are three ways in which hGH has been expressed for example, within the cell as inclusion bodies, in the periplasmic space or as secretory protein which is out of the cell (U.S. Pat. No. 4,755,465).

The secretion of 22 kD hGH into the periplasm of E. coli has been reported the secretion of 22 kD hGH (Gray et al. 1985, 247-254; U.S. Pat. No. 5,279,947). The periplasm refers to a space between the inner membrane and the outer membrane of gram-negative bacteria including E. coli. In gram-negative bacteria, a precursor protein containing a signal sequence is necessary for membrane penetration and upon passing the inner membrane the secretory signal is cleaved off. The protein is then processed into the matured protein by losing its secretory signal. There are several cloning patents reported so far (list has given below) which have helped to plan our strategy of hGH cloning unique to our laboratory.

Recently, it has become possible to produce the human growth hormone intracellular, extracellularly or in the periplasm by means of recombinant DNA technology in which a gene of hGH is expressed in a microorganism as a host (U.S. Pat. Nos. 5,047,333, 4,755,465, 4,604,359 and 4,601,980).

In situ post-translational modification with various enzymes for example Factor Xa, Enterokinase, Renin, or specific chemicals like CNBr, was also another area which has been looked upon where the mature hGH is isolated from either its chimeric protein part or from its extended N-terminal part. This enables its easy separation and purification of the total protein by means of appropriate chromatographic techniques from rest of the host protein. The impurity profile of purified hGH may directly depend on the choice of in situ post-translational modification.

There isn't a prior art so close to the invention disclosed herein. The teachings of the patent prior art, which are somewhat relevant, have been summarized below.

Here, in U.S. Pat. No. 3,853,832, the patent claims a method of producing a synthetic human growth promoting substances and is not related to inventive aspect of the present invention. It deals with polypeptide of 188 amino acid whereas human hGH has 191 amino acids. It teaches the introduction of sulphhydryl groups, oxidation and talks about their position. Present invention is related to novel approach of producing hGH by cloning of cDNA. U.S. Pat. No. 5,955,346 deals with nucleotide sequence encoding variant of human prolactin. The only similarity is it deals with protein.

U.S. Pat. No. 4,446,235 teaches a method of obtaining cDNA encoding a desired polypeptide and involves probing cloned genomic DNA to obtain the genomic sections and uses COS cell vectors. Therefore it doesn't teach what is taught by the present invention.

U.S. Pat. No. 4,665,160 claims the sequence of amino acids as are present on hGH-V and doesn't teach about cloning of cDNA or use of isoform-derived chimera or novel walk which is the novelty of the present invention. Present invention is related to production of hGH from hGH-NV.

U.S. Pat. No. 4,670,393 claims the replicable clone vehicle comprising arm inserted DNA sequence and enlists the sequence of amino acids whereas the present invention is related to production of hGH by a novel technique wherein a concept of chimera is exploited for the first time. U.S. Pat. No. 5,849,535 claims a variant of hGH and therefore it doesn't teach the present invention. U.S. Pat. No. 5,597,709 also claims a method for producing the human growth hormone variants by recombinant DNA technique from wild-type hGH which mainly focuses on the hGH-V but not on the pituitary derived hGH-N unlike the present invention. GB2055382A teaches use of pituitary hormonal fragments in synthesis of hGH. It teaches to combine naturally occurring and synthetic portions to get hGH using bacterial expression system. It is classically different from cloning of chimera of two isomers, which is the present invention. It talks about cloning vehicle and cloning vectors which are different.

U.S. Pat. No. 5,496,713 teaches the method to produce hGH in periplasmic space, which amounts to secretory production method. The present invention deals with a method of production, which is within the cell, well inside the wall and therefore is fundamentally different. U.S. Pat. No. 5,789,199 also teaches a technique to produce the heterologous polypeptides in bacterial periplasm. U.S. Pat. No. 5,047,333 teaches a method to produce naturally occurring hGH in *Bacillus* cell therefore it is different as in the present invention. The technique used in the present invention is novel and the host cell used is not *Bacillus* and the inventive concept is different than U.S. Pat. No. 5,047,333.

U.S. Pat. No. 4,859,600 claims of making a recombinant prokaryotic host cell containing hGH, the amino acid sequence of which consists of the amino acid sequence of naturally occurring hGH, which is free of other proteins associated with its native environment and is free of mature hGH having an extraneous N-terminal methionine, and which was produced by said recombinant prokaryotic host. U.S. Pat. No. 5,618,697 teaches a process of producing hGH where the construct contains a amino-terminal extension with a negatively charged amino acid sequence for easier downstream process.

U.S. Pat. No. 4,601,980 mainly talks about the downstream process to obtain the polypeptide produced and therefore deals with the aspects of fermentation and purification which is not the subject of the present invention.

U.S. Pat. No. 4,755,465 and several other patents teach, reveal and describe aspects of presence of methionine at N terminus and the advantages thereof and don't teach the present invention. U.S. Pat. No. 5,633,352 shows steps involves in the biosynthesis of hGH from pituitary derived hGH. A variant of a native human growth hormone with altered binding properties was shown in U.S. Pat. No. 5,688,666 by substituting a set of amino acids.

U.S. Pat. No. 5,635,604 shows a substantially pure amino-terminal extended hGH wherein X is a charged amino acid sequence having at least two amino acids and wherein the N-terminal amino acid of X is a negatively charged amino acid, other than Lys and Arg.

U.S. Pat. No. 6,436,674/EP0974654 teaches us about an efficient cloning method in *E. coli* and *Salmonella* where human growth hormone is targeted to the periplasmic space using a secretory signal peptide. Preferred method is secretory as per this invention because isolation and purification is rendered easy due to low level of impure proteins in periplasm as stated by the inventor.

In EP0587427 a process to produce 20K hGH is described using a novel neutral protease from *Bacillus amyloliquefaciens*. The process is secretory where this hGH is secreted into the bacterial periplasm. Another patent JP61224988 talks about a recombinant plasmid of *E. coli* for amplification of 20K hGH cDNA. In contrast JP61202689 describes an extraction process of growth hormone from human pituitary tissue and its subsequent processes.

EP0489711 describes the process to produce hGH having amino acid sequences of naturally occurring hGH. The process is characterized by the presence of Met at the N-terminus of the $1^{st}$ polypeptide produced.

Above referred citations either deal with secretory processes or with methionine characterized larger polypeptide or use of human pituitary and human placenta cDNA isoforms for producing hGH. However none of these documents describe a technique to use human placenta and pituitary hGH cDNA isoforms to derive hGH-NV cDNA, chimera, further to obtain an expressible construct of the chimera derived SEQ ID NO:5 which is linked with a strech of non-GC rich sequences in duplicate to subsequently produce 22K hGH which is identical in amino acid sequence to pituitary hGH, with better transcript secondary stretch than hGH-N (wild type). The unique construct and the better expression of the matured hGH is an inventive step of the present invention.

OBJECTS OF THE INVENTION

An object of the present invention is to provide a novel hGH-NV cDNA chimera as shown in SEQ ID NO: 3 encoding human growth hormone.

Another object of the present invention is to provide a plasmid vector pGEHNV containing novel hGH-NV cDNA chimera.

Yet another object of the present invention is to provide recombinant *E. coli* cells containing recombinant plasmid vector.

Still another object of the present invention provides a expressible construct of the chimera derived SEQ ID NO: 5 linked with a stretch of non GC rich sequences in duplicate.

Still yet another object of the invention is to provide recombinant *E. coli* cells containing a plasmid expression vector pABGH2.

Another object of the invention is to provide a process for the preparation of novel hGH-NV cDNA chimera.

SUMMARY

The present invention primarily relates to the novel hGH-NV cDNA chimera as shown in SEQ ID NO: 3 encoding human growth hormone derived from two distinct cDNA isoforms obtained from pituitary and placenta RNA and the invention also relates to a process for obtaining the said novel chimera involving the step of amplification by reverse transcription using gene specific primers, cloning the amplified cDNA isoforms, digesting the cloned cDNA isoforms at specific restriction endonuclease site followed by replacing in digested cDNA isoforms hGH-V fragment specific region by hGH-N fragment to obtain hGH-NV cDNA chimera. Further the invention relates to the use of hGH-NV cDNA chimera to obtain an expressible construct to produce mature human growth hormone.

BRIEF DESCRIPTION OF ACCOMPANYING DRAWINGS

The manner in which the objects and advantages of the invention may be obtained will appear more fully from the detailed description and the accompanying drawings, which are as follows:

FIG. 1 depicts the cDNA sequences of hGH isoform hGH-V and hGH-N in comparison with the hGH-NV chimeric construct.

FIG. 2 shows amino acid comparison of hGH-V (SEQ ID NO: 10), hGH-N (SEQ ID NO: 11) and hGH-NV (SEQ ID NO: 14).

Figure 5A:
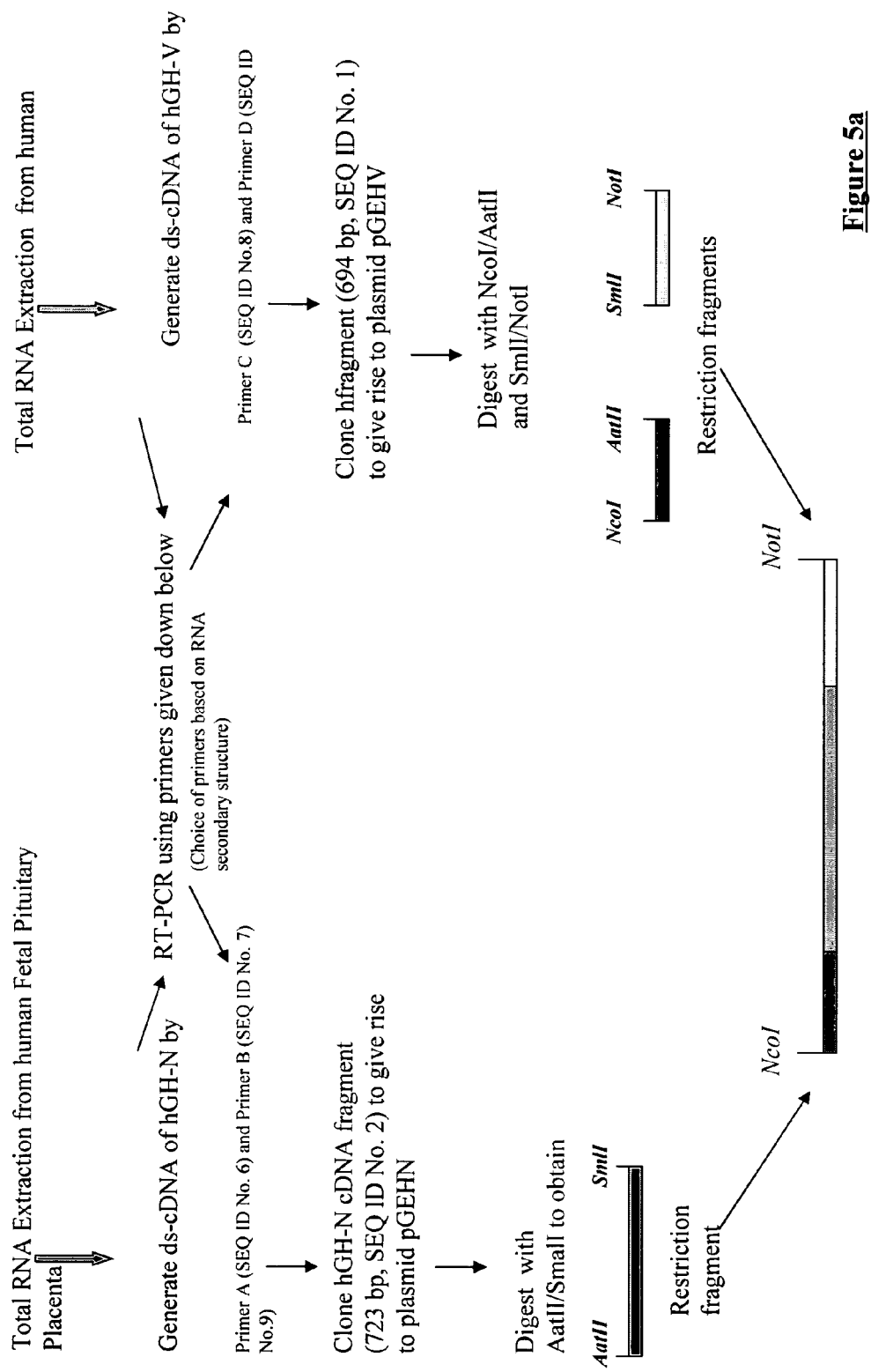

FIG. 5a schematic representation of the sequence of steps involved in making of hGH-NV chimera (SEQ ID NO: 3) and cloning to obtain pGEHNV plasmid.

Figure 5B:
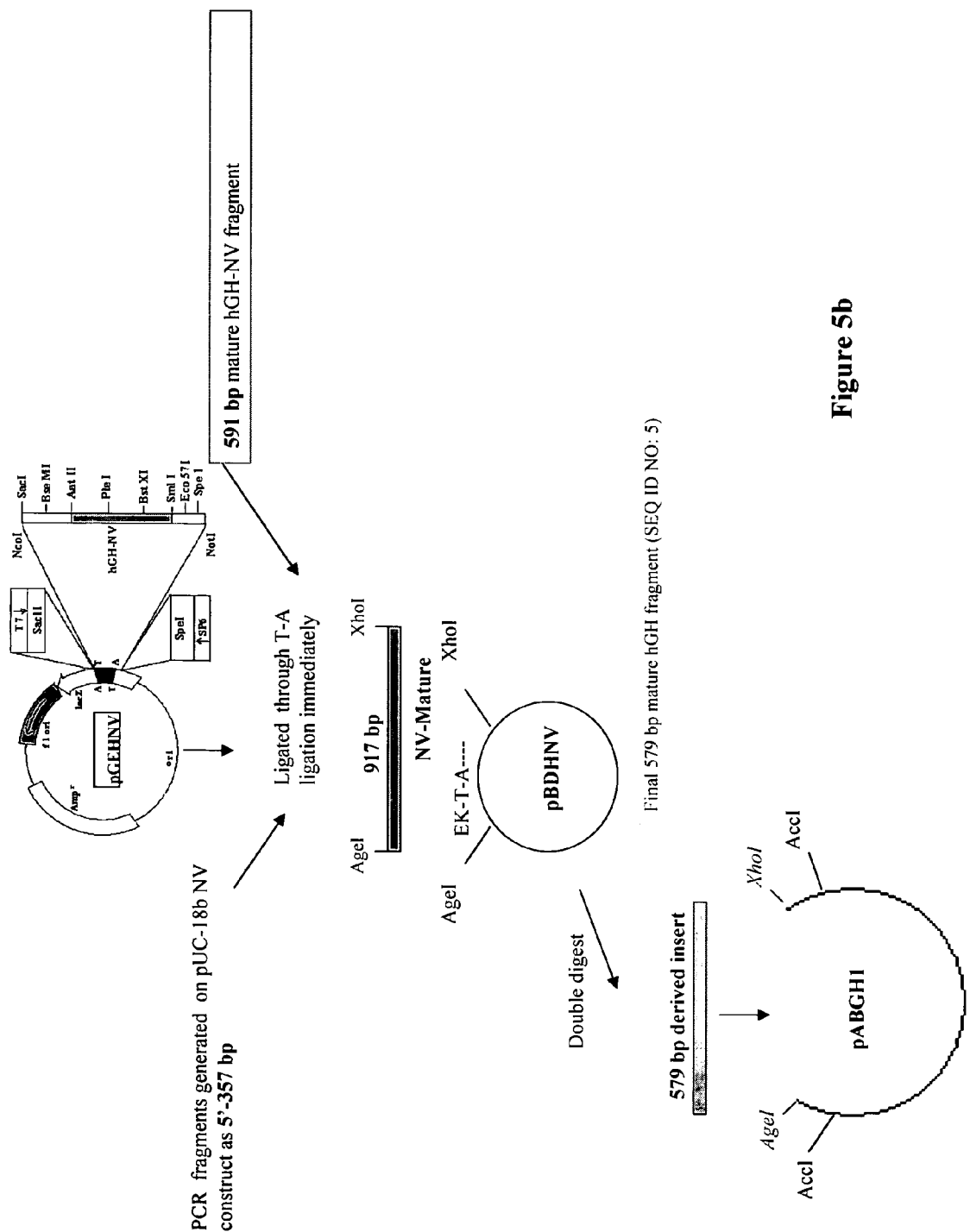

FIG. 5b shows the Flow chart of cloning strategy of chimeric hGH into ara-inducible vector to construct the plasmid clone pABGH1.

Figure 6:
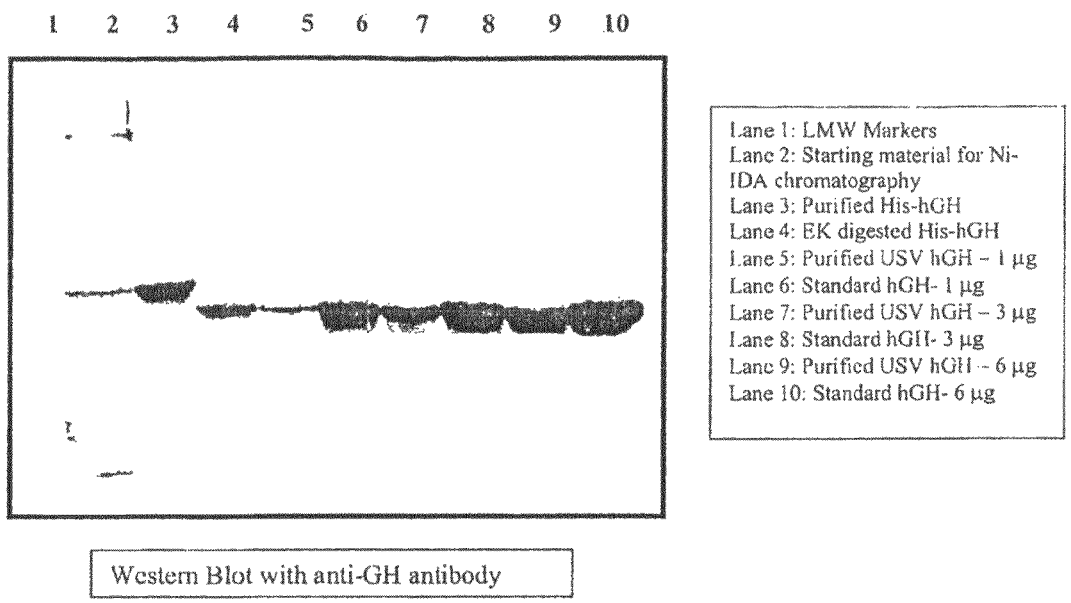

FIG. 6 illustrates the steps involved in achieving His-tagged hGH and subsequently the pure form of hGH from the lysate grown in the fermenter with a Western using anti-hGH antibody.

Figure 7:
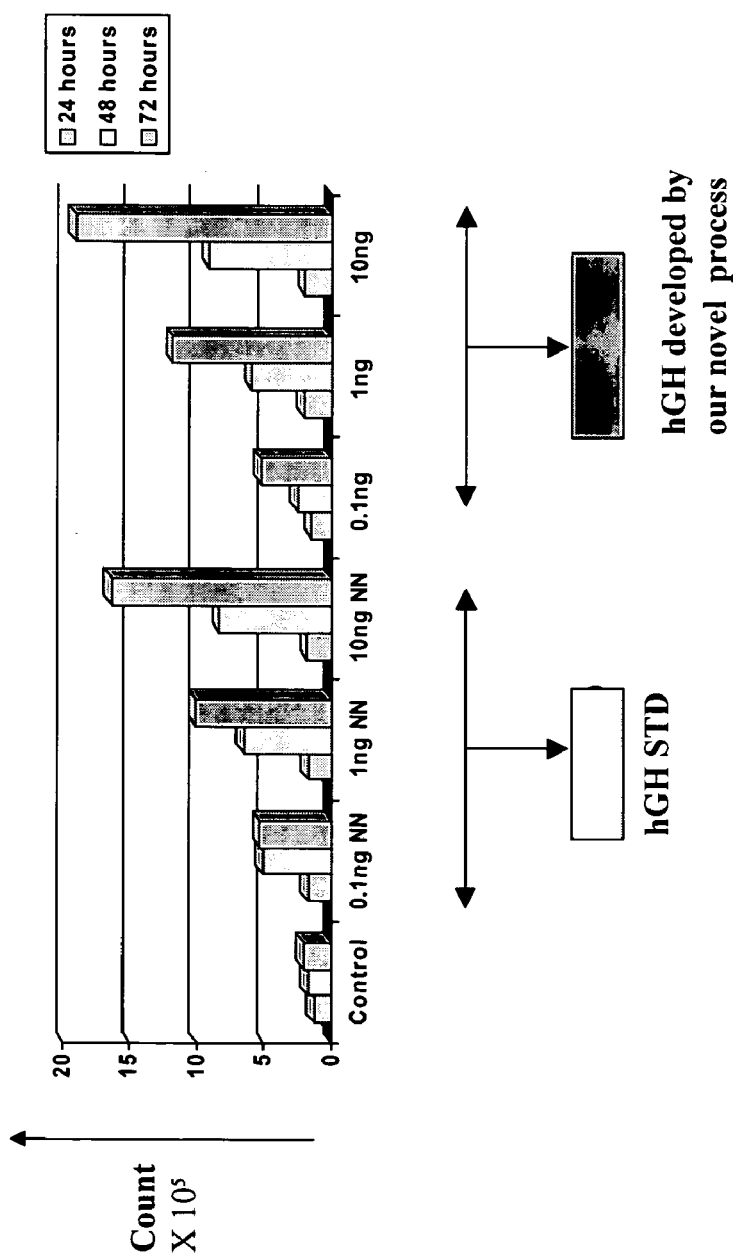

FIG. 7 shows the levels of bioactivity of the recombinant hGH compared to the commercial Norditropin.

Figure 8:
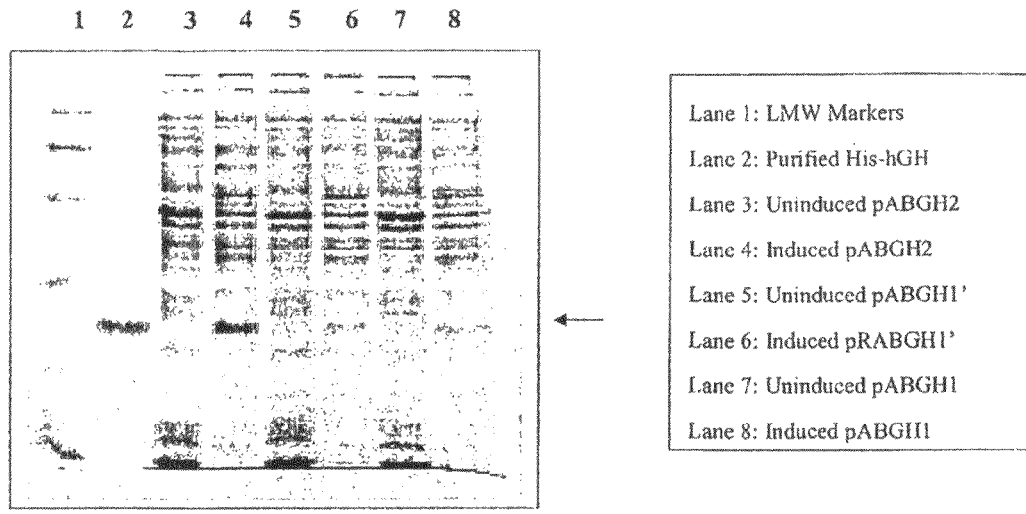

FIG. 8 shows the difference in hGH expression level between hGH #1 (pABGH1) and hGH #2 (pABGH2) clones by arabinose-induced expression in Coomassie (Stained Gel. Uninduced clones have taken as controls.

Here, pABGH1' refers Pituitary cDNA derived hGH (Chen et al., 1989, lane 5 & 6) clone, pABGH1 (lane 7 & 8) refers chimeric hGH-NV derived synthetic hGH clone and pABGH2 (lane 3 & 4) refers the later insert in duplicates.

DETAILED DESCRIPTION

Preferred Embodiments

Accordingly, the present invention relates to a novel hGH-NV cDNA chimera as shown in SEQ ID NO: 3.

An embodiment of the present invention provides plasmid vector pGEHNV containing SEQ ID NO: 3.

Another embodiment of the present invention provides a recombinant E. coli cell containing a plasmid vector pGEHNV comprising SEQ ID NO: 3.

An embodiment of the present invention relates to a process of obtaining novel hGH-NV cDNA chimera which encodes human Growth Hormone, the said process comprising steps of:
a) isolating the total RNA from human placenta and pituitary,
b) amplifying the respective cDNA isoforms, hGH-V from human placenta RNA and hGH-N from pituitary RNA of step (a) by reverse transcription using gene-specific primers selected from SEQ ID NO: 6, SEQ ID NO: 7, SEQ ID NO: 8 and SEQ ID No: 9,
c) cloning of the amplified cDNA isoforms hGH-V and hGH-N of step (b),
d) comparing the restriction endonuclease map of both the cloned cDNA isoforms of step (c) according to their inframe translated ORF sequence,
e) digesting the cloned cDNA isoforms of step (c) at specific restriction endonuclease sites,
f) replacing in digested cDNA isoforms of step (e) the hGH-V fragment specific regions by hGH-N fragment at specific restriction endonuclease sites (as mentioned in step e) by ligation to obtain the desired specific combinations of hGH-NV cDNA chimera, and
g) cloning of hGH-NV cDNA chimera as shown in SEQ ID NO:3.

Another embodiment of the present invention wherein the portions from the isoforms are put in specific combination for developing the cDNA fragment template of hGH for better codon usage.

Yet another embodiment of the present invention provides the use of desired specific combinations of hGH-NV cDNA chimera are 1-62 bp, 63-587 bp and 588-728 bp as shown in SEQ ID NO:3.

Still another embodiment of the present invention provides the use of restriction endonuclease are selected from BseMI, AatII, EcoNI, PleI, BstXI, EheI, SmlI, and SmaI.

Still yet another embodiment of the present invention generates matured hGH cDNA as shown in SEQ ID NO: 5 from novel hGH-NV cDNA chimera An embodiment of the present invention provides SEQ ID NO: 5 generated by cDNA amplification using gene-specific primers.

Another embodiment of the present invention the use of gene specific primers selected from SEQ ID NO: 17, SEQ ID NO: 18, SEQ ID NO: 19, SEQ ID NO: 20, SEQ ID NO: 21 and SEQ ID NO: 22.

Yet another embodiment of the present invention provides an expressible construct of the chimera-derived SEQ ID NO: 5 is linked with a stretch of non-GC rich sequences.

Still another embodiment of the present invention wherein the sequence of chimera-derived SEQ ID NO: 5 linked with a stretch of non-GC rich sequences is duplicated.

Still yet another embodiment of the present invention provides a plasmid expression vector pABGH2 containing chimera derived mature cDNA sequence as shown in SEQ ID NO: 5

Still another embodiment of the present invention provides a recombinant E. coli cell containing the plasmid pABGH2 for the production of the mature human growth hormone.

Significance of the Cloning Methods and Difficulty:

A. Placental mRNA and Availability of Tissue

Surprisingly, we have found that the gene for hGH (i.e., a gene coding for the 191 amino acids of the mature protein and the 26 amino acids of its signal peptide), which is expressed all-along to give pre-hGH in gram-negative bacteria, is similar in length to pre-hGH of the placental counterpart.

The growth hormone is synthesized in the form of a precursor, which is then produced in the anterior lobe of the hypophysis throughout the life of an individual, and in greater quantities during the pre-adult period and once processed is secreted from the cell.

Until a few years ago, the only source of the hormone was the hypophyses of corpses from which it was extracted at low yields by a complex and expensive method.

Figure 3:
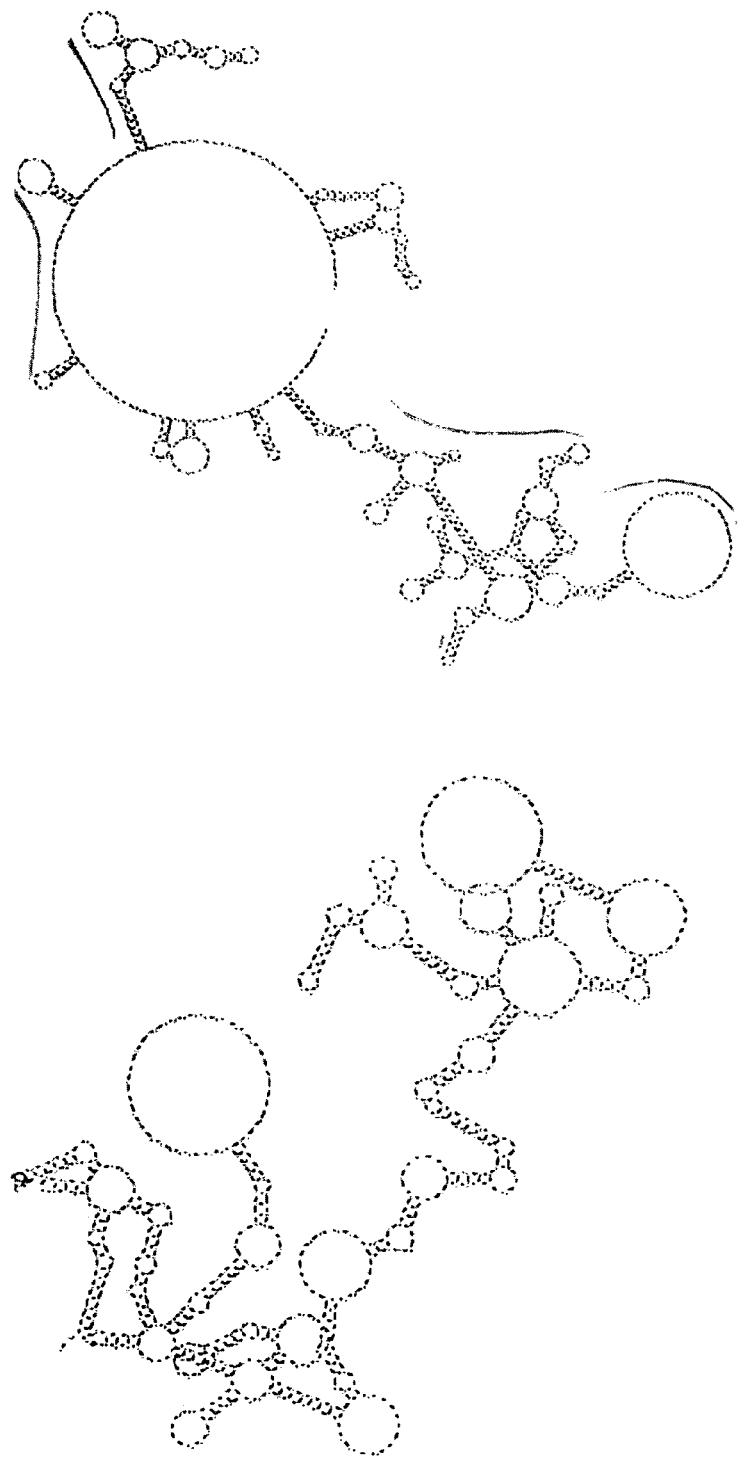
FIG. 3 shows a comparison of the folded RNA secondary structure based on hGH-N and hGH-NV sequences. The min energy of both (hGH-N and hGH-NV ORF Seq.) although is comparable, they greatly differ in their RNA secondary structure due to their sequence difference.

Hence, our present invention is essentially very helpful where placental mRNA as well as pituitary mRNA is the starting point of the cloning process of hGH-N analog hGH-NV. Five of hGH-V cDNAs represent mRNAs spliced and processed in a pattern analogous to that of the highly homologous human growth hormone and human chorionic somatomammotropin gene transcripts (Cooke et al., 1988). Moreover, stability of the placental mRNA during isolation also should be accounted. The cloning process gives a certain degree of freedom in shopping for codon usage in the final construct. The portion of hGH-V in hGH-NV was aimed to give better mRNA secondary structure than hGH-N (FIG. 3).

B. Cloning of Placental cDNA Constructs

For the first time we have attempted cloning of hGH-N analog isoform via cloning of hGH-V cDNA, despite the fact that these genes are expressed selectively in two different tissues under differential hormonal control (Parks et al., 1989). The hGH-N gene is transcribed only in somatotrophic cells of the anterior pituitary and the hCS-A and -B genes only in placental trophoblasts. Alternative splicing of the primary hGH-N gene transcription product (DeNoto et al., 1981) generates two mRNA species that respectively encode the human GH (22K form) and a somatotropin variant (20K form), which has amino acid residues deleted from hGH (Singh et al., 1974).

C. Basic Homology

Our present invention is primarily based upon the existence of variants of human growth hormone in the same chromosome locus, in particular, a representative gene coding for a hGH variant protein and containing 4-5 intervening genes. We have taken a unique choice to clone cDNA through cloning of hGH isoforms e.g., hGH-V, hCS.

Use of isoform of mRNA as the starting material for cloning and relevant enzymatic match site for getting pure form and suitable manipulation of ORF for high yield.

Strategy to shuffle between two isoforms' full length cDNA for cloning and introducing a change in specific amino acids' wobble sequence in the target cDNA, is the novelty of this invention.

A recombinant method of cloning tandem cassettes of the encoding region in expressible plasmid for high yield purified product (U.S. Pat. Nos. 5,955,323; 5,279,947; 4,859,765) also has been reported.

Construction of a Synthetic cDNA

The objective was to have the full-length chimera (from all possible combination of choice of chimera of hGH-NV (hGH-N analog from hGH-V isoform, FIG. 5) with its 26 aa signal sequence into a better promoter-controlled E. coli expressible system. This clone was used as a template to switch from the full length chimeric ORF to mature ORF of its synthetic form with a unique change in the wobble sequence of two amino acids with an authentic restriction enzyme site introduced.

In bacteria, inducible promoter-ribosome binding site (rbs) expression elements are generally utilized for high level heterologous gene expression. Plasmids carrying the said promoter-rbs expression elements and encoding genetic information for direct high-level expression of heterologous proteins, the ORF of the gene of interest can be constructed under the control of these above-mentioned regulatory elements. Moreover, expression vector system is also including affinity tags and a specific cleavage site immediately after the mature cDNA sequence to provide a desirable and easier purification system of the bacterially produced heterologous proteins by said recombinant microorganisms.

The expression of the cDNA insert is under control of an inducible ara C promoter, starting with ATG codon of vector's NcoI site & cleavage of the fusion protein with Enterokinase specific cleavage site (FIGS. 5a, 5b). The recombinant plasmid was used to transform E. coli TOP10 and selected as ampicillin resistant colonies. Induction of the protein was done by addition of L-arabinose in the medium at the log phase of bacterial growth and continued for 6 hrs. The detectable fusion protein was cleaved at the specific enzyme cleavage site and showed the correct molecular wt. size with the natural biological activity. DNA encoding human somatostatin, preproinsulin, proinsulin, insulin A chain, insulin B chain or bovine or human growth hormone, LH, ACTH, and pancreatic polypeptide a majority of codons preferred by microbial genome was inserted into a plasmid for expression in a microorganism.

Isolation of Human Placental mRNA

Total RNA was isolated from human placenta using by guanidium thiocyanate method by standard procedure (Ausuble et al., 1987). Poly (A$^+$) RNA was purified by affinity chromatography on Oligo (dT) cellulose. The mRNA was separated by oligo (dT) cellulose affinity chromatography from the total RNA, which was homogenized as described by Promega Total RNA Isolation Systems' protocol (Cat. # Z51110). This resulting mRNA was then used for generating $1^{st}$-strand by using a standardized method with the help of AMV transcriptase. Nor-specific interactions between strands were reduced using RNase H and RNase A, followed by purification of the $1^{st}$-strand DNA (20 ng/µl) using phenol/chloroform/isoamyl alcohol and 70% ethanol wash.

Total RNA was isolated from human placenta by using "RNAgents for Total RNA Isolation Systems" (Promega, Cat. # Z51110). Approximately 2 gms of tissues were processed each time. Total RNA pellet was resuspended in 1 ml nuclease-free water and stored at −70° C. Total RNA concentration was around to 4 µg/µl. Polyadenylated RNA was pooled with the help of oligo (dT)$_{8-12}$ and oligo (dT)$_{10}$ beads from total RNA. 1 µg of total RNA was used for each reaction. Polyadenylated RNA was reverse-transcribed into single-stranded $1^{st}$-strand complementary DNA using AMV reverse transcriptase at 42° C. for 1 hr. Optimum concentration of $1^{st}$-strand cDNA was in the range of 20 ng/µl.

Synthesis and Cloning of cDNA

Figure 1A:
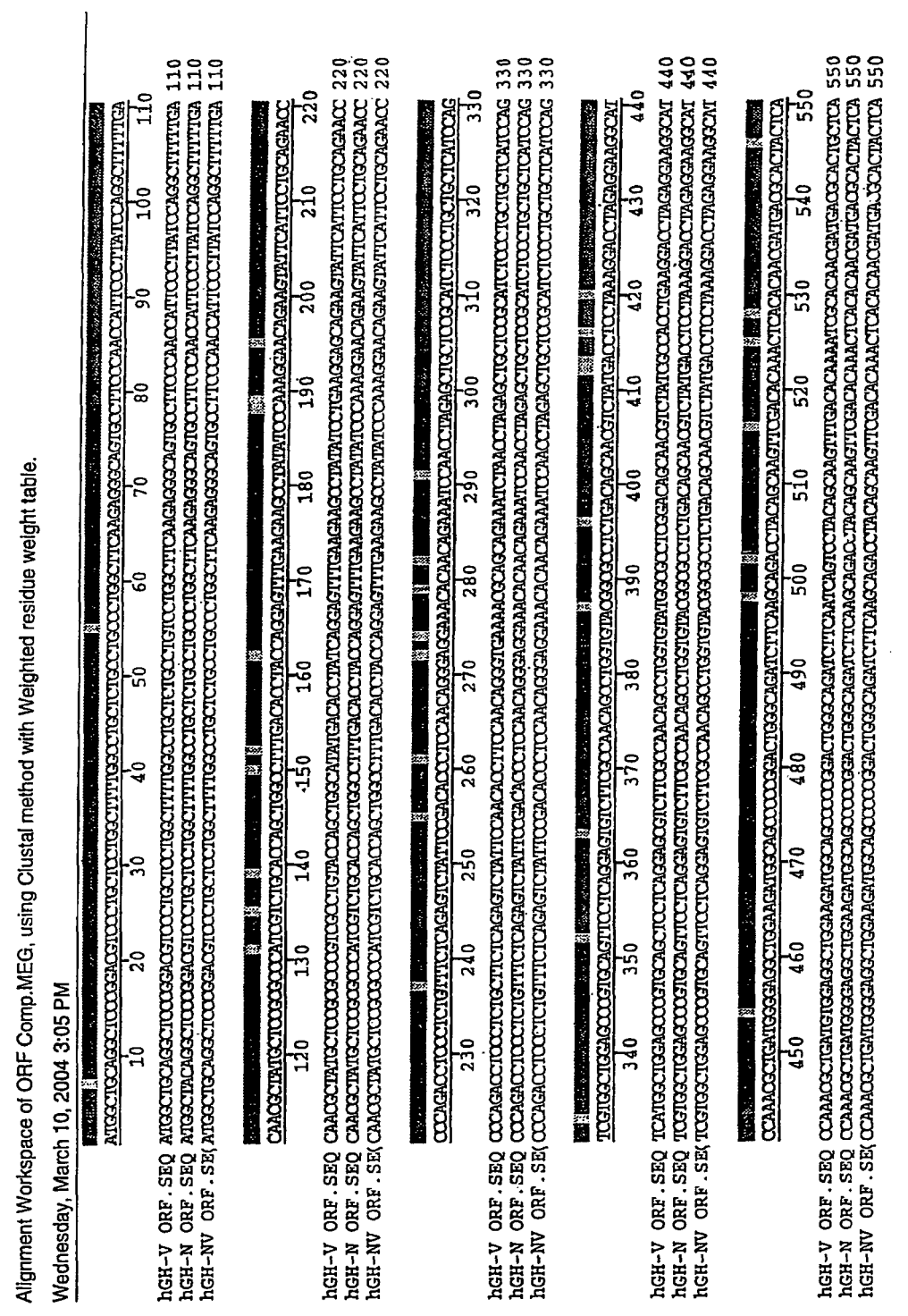
Figure 1B:
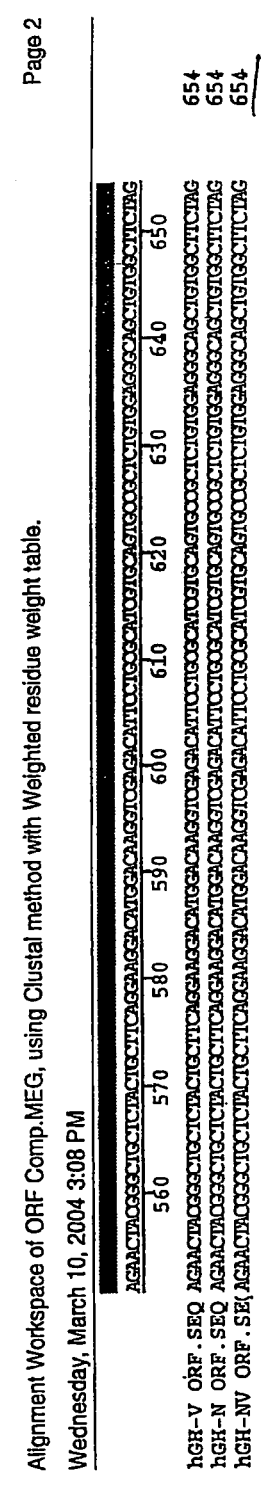

Oligo (dT)$_{12-18}$ beads were used to purify and select the stable poly (A$^+$) RNA (messenger RNA) which was used to prime for reverse transcription to generate $1^{st}$-strand cDNA following standard RT-PCR technique (FIGS. 1, 2, 5a).

Reverse Transcription and $1^{st}$-Strand Synthesis:

For the transcription reaction set up 1.0 ug RNA/mRNA, 0.5 ug Primer (oligo dT), nuclease free water and heat at 70° C. for 5 min then chill on ice for 5 min. Microlfuge for 5 secs to settle materials. Then add serially: nuclease free water, RT buffer (5×), dNTP mix (12.5 mM) Ribonuclease inhibitor (1:2 dilution of 40 U/ul) and Sodium Pyrophosphate (40 mM, 4 mM Final conc.), mix gently and then prewarm the mix at 42° C. for 2 min, then AMV Reverse Transcriptase (RT) (10 U/ul). Mix well gently, and then leave at 42° C./1.0 hr (RT reaction) and then heat at 75° C. for 10 min (inactivation of RT). Add 1.0 Units RNase A/tube and incubate at 25° C. for 30 min. then added 0.5 units of RNase H to each reaction tube and incubate 30 min at 37° C.

Next, to clean up the 1$^{st}$ strand cDNA add Tris-Cl/1.0 mM EDTA (pH 5-7.5). Then add buffered phenol (pH 5-8.0)-Chloroform-Isoamyl alcohol, vortex and spin ~14,000 rpm in the microfuge centrifuge. Transfer aqueous phase to a fresh tube and add 3M Sodiumi Acetate (pH 3-7), mix well. Then add chilled 100% EtOH and leave at −70° C. followed by spinning at 14,000 rpm for 5 min. Wash pellet with EtOH by spinning at 14,000 rpm for 5 mia at 4° C. Then resuspend in nuclease free water.

Standard PCR amplification was done using Taq polymerase to make double-stranded cDNA prior to clone the gene of interest into an appropriate vector of choice. Here, mix all the ingredients e.g. buffers, primers, 1$^{st}$-strand cDNA, 2 mM dNTP, enzyme and heat at 94° C. 1 min in the thermal cycler for denaturation. Anneal at 2-4° C. below the Tm of the primers and then extension at 72° C. Go through total of 45 cycles for amplification. Then run the PCR reaction on 0.8%-2% agarose gel as required.

Double-stranded cDNAs are synthesized by following standard PCR amplification technique by using Taq polymerase. This fragment of interest was then directly cloned into a pUC-18-based TA-cloning vector. A bacterial strain JM109 was selected for generating transformants for further work.

Cloning Technique

Cloning and construction of the PCR Taq polymerase amplified double stranded fragment with adenine on both sides went directly into a TA-cloning vector (FIGS. 2, 5). Polyadenylated mRNA for hGH-V was prepared from placental and pituitary tissues. Total of 100 ng of 1$^{st}$-strand cDNA was prepared from 5 μg of this total RNA. 20 ng of 1$^{st}$-strand was used as the template for annealing gene-specific primers, namely, Primer A (SEQ ID NO: 6); Primer B (SEQ ID NO: 7); Primer C (SEQ ID NO: 8); Primer D (SEQ ID) NO: 9) to amplify 694 bp (SEQ ID NO: 1) hGH-V fragments and 723 bp (SEQ ID NO: 2) hGH-N fragments. These double-stranded fragments with A-tailed at both 5'- and 3'-ends were directly cloned into a pUC-18-based cloning vector in presence of E. coli T4 DNA ligase to obtain pGEHV and pGEHN construct. These clones further were checked separately by double digesting with NcoI/NotI, NcoI/PstI. Further, restriction enzyme map analyses were done using NcoI/RsaI, BstXI, EcoRI/SmlI, SmaI, EcoRI/BglII, HgaI, which has determined the fidelity of the cDNA PCR fragment.

Figure 4:
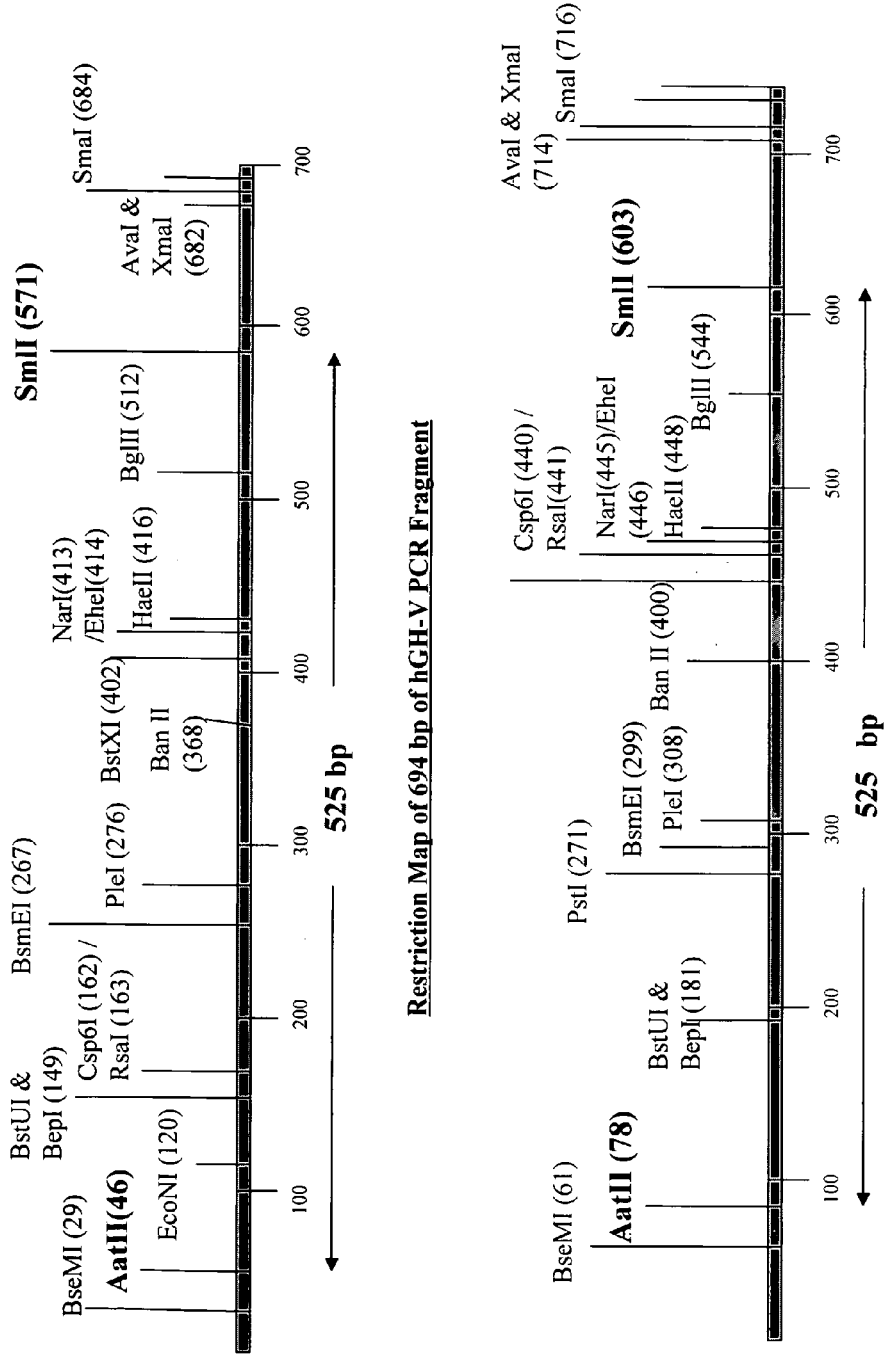
FIG. 4 shows schematic representation of the restriction enzyme sites of hGH-N and hGH-V for producing the chimera hGH-NV.

Walking from a hGH-V Plasmid Construct to a hGH-N Plasmid Construct and Making a Possible Template Chimeric cDNA Construct In making hGH-chimeric construct, hGH-V (SEQ ID NO: 1) and hGH-N (SEQ ID NO: 2) were cloned separately from placenta and fetal pituitary, respectively, into a cloning vector. This was followed by replacement of hGH-V fragment's specific regions by E. coli-able hGH-N using several restriction enzymes to give synthetic hGH-NV (SEQ ID NO: 3) (FIGS. 1, 4, 5a).

A thorough restriction analysis of both cDNAs was done using the unique restriction enzymes. Restriction enzyme map of both the clones was compared (FIG. 4) and analyzed to select a unique strategy to replace hGH-V with hGH-N at certain regions using restriction enzyme digestion. NcoI, NotI, AatII and SmlI were the enzymes used to make the hGH-NV chimera in making the chimera of hGH NV there are no primers or PCR amplification was done to avoid mutations. Only restriction enzyme digestion was done on both hGH-N and hGH-V fragment to shuffle the AatII and SmlI hGH-V 525 bp cDNA fragment portion with hGH-N cDNA The final construct of hGH-NV chimera of 728 bp (SEQ ID NO:3) was made in pUC-18 based vector within NcoI/NotI enzyme sites.

Cloning of hGH-N in the modified form using hGH-V cDNA was for better E. coli expression. For that purpose, hGH-V (SEQ ID NO: 1) from placenta and hGH-N (SEQ ID NO: 2) from fetal pituitary were previously cloned into the pUC-18 TA-cloning vectors and then using the chimera (SEQ ID NO: 3) as template, hGH-NV mature cDNA was subcloned into arabinose inducible E. coli expression vector immediately after the Enterokinase cleavage site (FIGS. 5a, b).

Cloning of hGH-NV mature fragment (591 bp, SEQ ID NO: 4) into pBAD-HisA expression vector was done by PCR amplification on the mature peptide portion of hGH-NV chimera (728 bp, SEQ ID NO: 3) excluding the 26 amino acid sequences by gene specific primer which gives the expected PCR product of 591 bp (SEQ ID NO: 4). For amplification of 591 bp mature hGH-NV fragment, Primer E (SEQ ID NO: 12) and Primer F (SEQ ID NO:13) was used for PCR amplification. Gene-specific primer pairs (Primers E & F) are shown in FIG. 5 for amplification of 591 bp mature hGH-NV fragment, Primer E (SEQ ID NO: 12) and Primer F (SEQ ID NO: 13). The vector portion was amplified from plasmid (pBAD/HisA, Invitrogen) to give rise to a 357 bp fragment by the primer pair, primer Q (SEQ ID NO: 15) and primer R (SEQ ID NO: 16).

The advantage of having the difference in amino acids (total-13) in hGH-V from hGH-N has taken into consideration where the changes are done on hGH-V clone in such a way so that those amino acids are replaced with the hGH-NV cDNA stretch. Consequently, these changes also made a E. coli-able modified hGH cDNA product keeping its expression efficiency in mind. The selection of hGH-NV fragments is based on codon usage and RNA secondary structure rationale. In the final hGH-NV chimeric construct (728 bp, SEQ ID NO:3), the first 8 amino acids out of 26 amino acids signal peptide are from hGH-V cDNA, in the 3$^{rd}$ amino acid alanine differs from hGH-N 3$^{rd}$ amino acid. From 9-192 amino acids are borrowed from hGH-N cDNA and 193-218 amino acids are again borrowed from hGH-V cDNA Here, we had taken the previous pGEHV containing SEQ ID NO: 1 and pGEHN containing SEQ ID NO: 2 full-length cDNA clones, and digested separately with unique restriction enzymes to replace the hGH-V fragment's specific regions with E. coli-able hGH-N portions. Then the final hGH-NV chimera was cloned back into pUC-18 based TA-cloning vector in between NcoI/NotI restriction enzymes site, pGEHNV. Restriction analysis was done to confirm the ligated hGH-NV chimera within pUC-based TA-cloning vector.

For further modifications, hGH-NV chimeric construct (pGEHNV) was used as the template for generation of cDNA with modified wobble sequence for similar amino acids and addition of a unique RE site (BsrGI) but keeping the rest of the sequence similar to the pituitary form of hGH (pABGH1). Finally, the mature hGH ORF of the modified form (a unique restriction site, BsrGI has been introduced) was cloned into arabinose inducible E. coli expression vector just after EK cleavage site, the length of which was about 579 bp, (SEQ ID NO:5) hGH Clone #1(pABGH1) (FIG. 5b) using Primer E (SEQ ID NO: 12) and Primer F (SEQ ID NO:13). For comparison with the original pituitary cDNA expression, PCR product amplified using total RNA from fetal pituitary and cloned into ara-inducible vector immediately after EK cleavage site which has shown poor protein expression level of hGH compared to 579 bp synthetic one (SEQ ID NO:5, FIG. 8). This cDNA sequence derived from hGH-NV chimera was taken the choice of codon usage according to the degeneracy is maintained in E. coli for increasing the expression efficiency. As an effect we have seen the level of hGH expression in both the clones, even though the difference is not much (FIG. 8),e.g., going from hGH-V (SEQ ID NO:1) to hGH-N (SEQ ID NO:2) to finally hGH-NV chimera (SEQ ID NO: 3) has introduced few E. coli-able codons and the restriction site (BsrG1) introduction has changed the $3^{rd}$ codon of the amino acid as well (SEQ ID NO: 5) using Primers J-O of SEQ ID NO: 17-22 during cloning steps (FIG. 5b).

Details of Making of the hGH-NV Chimeric Construct

Original tissue source for total RNA extraction was taken from human fetal pituitary tissue for hGH-N and human placenta for hGH-V cDNA synthesis. Expected RT-PCR amplified cDNA products of hGH-N (723 bp, SEQ ID NO: 2) and hGH-V (694 bp, SEQ ID NO: 1) cDNAs were TA-ligated in pUC-18 based vector (FIG. 5a). A thorough restriction analysis of both cDNAs was done using the unique restriction enzymes (FIG. 4).

Step I. In making of hGH-NV chimeric cDNA form, pUC-18 based clones of hGH-V (#6 and #25) are double digested with NcoI/NotI which are the unique sites of pUC-18 based vector and absent within hGH-V 694 bp fragment (SEQ ID NO: 1). NcoI/NotI digested 720 bp fragment (identify on SEQ ID NO: 3) was gel-purified to isolate the 5' (55 bp) and 3'-ends (139 bp). The NcoI/NotI digested open pUC-18 based vectors (pGEHNV, 2941 bp) are also purified for future cloning (FIGS. 5a, b).

Step II. NcoI/NotI double digested 720 bp gel-purified fragment is digested again with AatII/SmlI to isolate 55 bp of 5'-end and 139 bp of 3'-end fragments from middle 525 bp AatII/SmlI fragment. This 525 bp hGH-V cDNA fragment was replaced with AatII/SmlI 525 bp hGH-N fragment by which 13 amino acids difference in human placental hGH-V from human pituitary isolated hGH-N was changed. HGH-V differs with hGH-N signal sequence in two amino acids (at the $3^{rd}$ and $19^{th}$) out of the 26 amino acids, whereas in hGH-NAV signal sequence the $3^{rd}$ amino acid matches with hGH-V but the $19^{th}$ one matches with hGH-N. Out of 165 amino acids 140 amino acids of hGH-NV including mature peptide is matching with hGH-N sequence where hGH-N differs with hGH-V mostly. The last 25 amino acids again are matching with hGH-V sequence.

At this step, a ligation reaction was done at 4° C. for overnight to ligate the 55 bp and 139 bp fragments at their corresponding restriction sites (FIG. 4) with sticky ends with the help of T4 DNA ligase.

A comparative restriction enzyme map of both the clones selected a unique strategy to replace hGH-V with hGH-NV at certain regions using restriction enzyme digestion (NcoI, NotI, AatII and SmlI) shows a full-length of 728 bp of ligated hGH-NV cDNA fragment (SEQ ID NO:3).

PCR amplification of the mature peptide portion of hGH-NV cDNA by gene-specific primer pairs given the expected PCR product of 591 bp (SEQ ID NO: 4, FIG. 5b). Gene-specific primer pairs (Primers E & F) are shown in FIG. 5 for amplification of 591 bp mature hGH-NV fragment, Primer E (SEQ ID NO: 12) and Primer F (SEQ ID NO: 13). The vector portion was amplified from plasmid (pBAD-HisA) to give rise to a 357 bp fragment by the primer pair, primer Q (SEQ ID NO: 15) and primer R (SEQ ID NO: 16). Primer E was selected in such a manner so that out of the first amino acid (TTC), Phenylalanine, the start of mature hGH TC (Primer E at 119 in SEQ ID NO: 3) was selected as first nucleotides. Primer F was selected at 681-694 in SEQ ID NO: 3 where the rest of the nucleotides were selected based on the ara-inducible vector which included XhoI restriction site for cloning. 591 bp sequence is shown below, where the position of the primers are defined within the box:

```
|TCCCAACCATTCCCTTATCCAGGC|TTTTTGACAACGCTATGCTCCGCGCCCATCGTCT

GCACCAGCTGGCCTTTGACACCTACCAGGAGTTTGAAGAAGCCTATATCCCAAAGG

AACAGAAGTATTCATTCCT

GCAGAACCCCCAGACCTCCCTCTGTTTCTCAGAGTCTATTCCGACACCCTCCAACAG

GGAGGAAACACAACAGAAATCCAACCTAGAGCTGCTCCGCATCTCCCTGCTGCTCA

TCCAGTCGTGGCTGGAGCC

CGTGCAGTTCCTCAGGAGTGTCTTCGCCAACAGCCTGGTGTACGGCGCCTCTGAC

AGCAACGTCTATGACCTCCTAAAGGACCTAGAGGAAGGCATCCAAACGCTGATGGG

GAGGCTGGAAGATGGCAGCCCCCGGACTGGGCAGATCTTCAAGCAGACCTACAGCA

AGTTCGACACAAACTCA

CACAACGATGACGCACTACTCAAGAACTACGGGCTGCTCTACTGCTTCAGGAAGGA

CATGGACAAGGTCGAGACATTCCTGCGCATCGTGCAGTGCCGCTCTGTGGAGGGCA

|GCTGTGGCTTCTAGTAAC|
```

XhoI
▼
|TCGAGTGGCCGC|

Restriction enzyme digestions of the hGH-NV mature clone of pBAD/HisA with NcoI/Eco24I, NheI/EheI, NcoI/XhoI, BshTI/XhoI/BstXI, BshTI/XhoI, NcoI/EcoRI, have given also the correct fragment sizes. Further analysis with NcoI/Bsh1236I, NcoI/PleI, NcoI/PstI, NcoI/BstXI, NcoI/EheI, NcoI/BglII, NcoI/Eco57I, PleI/XhoI, NcoI/PstI/EheI, Bsh1236I/BglII on the clone and on the NcoI/EcoRI digested gel-purified fragment.

Making A Unique Construct of Arabinose-Inducible hGH Clone

For optimization of hGH protein expression in *E. coli* a multimerization of the whole cassette containing promoter-insert-terminator sequence is tried to clone in the similar expression vector. To achieve this modification, hGH Clone #1, pABGH1 (hGH-NV derived synthetic single hGH insert, FIG. 5a) which has shown 5% of total *E. coli* expression, was taken as the template plasmid.

hGH Clone #1 (pABGH1) is digested with BshTI/EcoRI (unique sites at 74 and 977, respectively) and purify both the digested fragments, 3717 bp (FRAGMENT 1) and 903 bp (FRAGMENT 2) separately. Digest pABGH1 DNA with AccI (sites at 350, 1447, 3412) and EcoRI (site at 977), which gives rise to 627 bp, 470 bp, 1558 bp and 1965 bp. Then purify the 470 bp fragment (FRAGMENT 3). Set up another digestion of pABGH1 DNA with AccI (sites are mentioned above) and BshTI (site at 74), that gives rise to 276 bp, 1097 bp, 1282 bp and 1965 bp. Then purify the 1282 bp fragment (FRAGMENT 4). All the ligation reactions were incubated at room temperature for 1 hr then at 4° C. for overnight.

Ligate FRAGMENT 2 and FRAGMENT 3 to get 1373 bp FRAGMENT 5). Then ligate the FRAGMENT 5 with FRAGMENT 1 to get 5090 bp (FRAGMENT 6. Then ligate FRAGMENT 4 and FRAGMENT 2 separately to achieve 2185 bp (FRAGMENT 0. Finally, ligate FRAGMENT 6 and 7, which would give the completion of the modification of hGH clone #1 (pABGH1, 4620 bp) to hGH clone #2 (pABGH2, 7275 bp). Positive clones were analyzed by DNA extraction and restriction enzyme analysis with the unique sites e.g., PvuI to get the linearized pABGH2 of 7275 bp fragment as well as the duplicate restriction sites eg., EcoRI, BshTI. The exact length of the insert was 2655 bp which was duplicated and inserted as tandem cassettes in the ara-inducible expression vector immediately after the EK cleavage site. For further confirmation of the cassette, analysis was done by sequencing on the two fragments, 2655 bp and 4620 bp, after NcoI or BshTI digestion. This attempt in making of pABGH2 clone immediately reflected on the level of hGH expression by almost two fold increase (FIG. 8).

An attempt has been taken to increase the number of cassettes in the ara-inducible vector for even higher level of hGH expression. After making pABGH2 construct, addition of an extra cassette couldn't make the plasmid as a stable one. After two passages of the same culture, pABGH3, third insert cassette was lost which was sequenced and confirmed. pABGH2 was only the stable plasmid which even after two years and has been shown the stability also in the fermentor grown culture.

Purification of the Mature hGH from Fermenter Grown Cell Culture

Induced cell culture from the fermenter was used as the source of lysate material where recombinant hGH was obtained along with soluble *E. coli* proteins.

Purification of recombinant hGH (from pABGH1 and pABGH2 expression clone) was achieved through several unique steps of which was shown here by a corresponding Western Blot in FIGS. 6 and 8. The purified hGH was tested for biological activity, which had shown high efficacy compared to the commercial Norditropin standard from Novagen (FIG. 7).

Bioactivity of Growth Hormone:

Purified hGH was tested to check its bioactivity along with the commercial hGH (Norditropin, from Novagen). GH bioactivity is the target tissue response equivalent to that induced by a known standard with the assumption that stimulatory or inhibitory principles are the same in the serum as the comparison standard. It is known for quite sometime that lymphoma cells respond specifically to lactogenic hormones, including human Growth Hormone (GH) which is known for it's lactogenic activity. The method used for hGH bioassay was according to Tanaka's method (Tanaka et al. 1980, Ealey et al. 1995) with small modification. Nb-2, rat lymphoma cell line obtained as gift, was used for checking the biological activity of hGH. The Nb-2 cells have been routinely maintained in RPMI containing 10% Fetal Bovine Serum (FBS) and 10% Horse Serum (HS). Twenty-four hours prior to bioassay, cells were maintained in quiescent medium, RPMI 1640 containing 1% FBS and 10% Horse serum. At the time of assay, cells were washed and counted and the cell density was adjusted to $1 \times 10^5$ cells/ml using the plating medium, RPMI+10% Horse serum. The plating cell density was $1 \times 10^5$ cells/ml/well for 24 well plate. Different concentrations of standard and hGH produced as per the novel process of the present invention were added to cells and incubated in, 37° C., 5% $CO_2$ incubator for 24, 48 and 72 hours. The cells were counted after every 24, 48 and 72 hours using hemocytometer.

It was quite evident from the table 2 and histogram (FIG. 8) that there was dose dependent increase in cell number as function of time. The maximum cellular proliferation was obtained after 72 hours. The bioactivity of growth hormone produced as per novel process of the present invention was comparable with reference standard of growth hormone standard and was reproducible. The data in table 2 is a representation of at least 4 experiments.

The following examples are provided for illustration only and should not be construed to limit the scope of the present invention.

Example 1

Cloning Through Mutagenesis into the cDNA of Interest

Introduction of unique restriction enzyme site(s) or change at the codon level in the ORF region was done during synthesis of gene-specific primer(s). For example, this modification, mutation per se, on the cDNA was introduced on the human growth hormone using hGH-V and hGH-N published cDNA sequence as template. Sequence of the hGH-V cDNA is shown down below as an example where highlighted boxed regions are defining the site of upper (Primer A, SEQ ID NO: 6) and lower PCR primers (Primer B, SEQ ID NO: 7) selection site for PCR amplification of 694 bp hGH-V fragment (SEQ ID NO:1). Here, the position of the primer pair is shown to amplify 694 bp hGH-V fragment (SEQ ID NO: 1) from placental $1^{st}$-strand. Starting of ATG and the termination codon, TAG, are highlighted in different color within the same sequence region.

5'-
AGGATCCCAAGGCCCAACTCCCCGAACCACTCAGGGTC CTGTGGACAGCTCACCTA

GCGGCAATGG CTGCAGGCTCCCGGACGTCCCTGCTCCTGGCTTTTGGCCTGCTCTGC

CTGTCCTGGCTTCAAGAGGGCAGTGCCTTCCCAACCATTCCCTTATCCAGGCTTTTTG

ACAACGCTATGCTCCGCGCCCGTCGCCTGTACCAGCTGGCATATGACACCTATCAGG

AGTTTGAAGAAGCCTATATCCTGAA

GGAGCAGAAGTATTCATTCCTGCAGAACCCCCAGACCTCCCTCTGCTTCTCAGAGTC

TATT

CCAACACCTTCCAACAGGGTGAAAACGCAGCAGAAATCTAACCTAGAGCTGCTCCG

CATCTCC

CTGCTGCTCATCCAGTCATGGCTGGAGCCCGTGCAGCTCCTCAGGAGCGTCTTCGCC

AACAGCCTGGTGTATGGCGCCTCGGACAGCAACGTCTATCGCCACCTGAAGGACCT

AGAGGAAGGCATCCAAACGCTGATGTGGAGGCTGGAAGATGGCAGCCCCCGGACTG

GGCAGATCTTCAATCAGTCCTACAGCAAGTTTGACACAAAATCGCACAACGATGAC

GCACTGCTCAAGAACTACGGGCTGCTCTACTGCTTCAGGAAGGACATGGACAAGGT

CGAGACATTCCTGCGCATCGTGCAGTGCCGCTCTGTGGAGGGCAG CTGTGGCTTCTA

GCTGCCCGGGTGGCATC CCTGTGACCCCTCCCCAGTGCCTCTCCTGGTCGTGGAAGG

TGCTACTCCAGTGCCCACCAGCCTTGTCCTAATAAAATTAAGTTGCATCATTT -3'

Expected Product Length 694 bp (SEQ ID NO: 1).

During PCR amplification, introduction of restriction enzymes sites within the appropriate site at the 5'- and 3'-end of the cDNA was possible. These changes were utilized for cloning into a specific expression vector further. These mutations within the full-length cDNA, which has not affected the coding region e.g., putative hGH-V cDNA was amplified among others using the gene-specific primer pairs (Primers C&D; SEQ ID NOs: 8 & 9, Table 3).

Primers for hGH-V Amplification:

Example 2

Validation of the Putative Clones by Restriction Enzyme Analysis of a Locus

A DNA fragment of about 723 bp (hGH-N, SEQ ID NO:2) or 694 bp (hGH-V, SEQ ID NO:1) was obtained by double digesting pUC-18 based clones with restriction endonucleases SalI and XhoI at 20 µl total reaction set up. The reaction sample was run on 1% agarose gel to purify the band

| Primer Sequence (5' → 3') | Features | Length | Tm | Nucleotide position on the wild type sequence (Chen, et al. 1989) |
|---|---|---|---|---|
| ✓CTGTGGACAGCTCAGGTACCGGCAATGG (Primer C) SEQ ID NO: 8 | With KpnI site | 28 mer | 60.7° C. | 39-66 |
| ✓GATGGGATCCGAGCAGCTAGAAGCCACAG (Primer D) SEQ ID NO: 9 | With BamHI site | 29 mer | 60.7° C. | 571-600 | of interest by using MBI, Gel Extraction Kit, Cat. #K0513. The resulted 2-3 μl purified fragment then analysed for its restriction endonuclease map by digesting with six to seven unique cutters either in combination or as single (enzyme conc. was usually 10 U/μl), e.g. NcoI/NotI, KpnI/BamHI, BsrDI/SpeI, BglII/BamHI, NcoI/HgaI, NcoI/RsaI and EcoRI/BglII. Approximate fragment size was estimated from these restriction endonucleases enzyme digestion before analysis on agarose gel after running digested samples. Restriction endonuclease enzyme digestions also were checked to ascertain about the validity of the bacterial clones containing the insert of our interest. Here, the restriction endonuclease enzyme digestions were selected in such so that the distance of the insert from the vector enzyme sites is mapped and the orientation of the insert in 5' to 3' direction is known e.g., PvuI, SalI/EcoRI, Cfr10I, ApaLI, BshTI, AvaI, SspI, AccI, etc.

Example 3

Making 1$^{st}$-Strand and Codon Usage

In this invention, our interest lies in cloning of hGH-V from placenta and hGH-N from pituitary into an *E. coli* TA-cloning vector through Oligo-dT RT-PCR. To clone hGH-V, total RNA was extracted from human placenta. Gene-specific upstream and downstream primers are designed according to the hGH-V cDNA sequence (Chen et al., 1989). RT-PCR was done on oligo dT$_{(8+12)}$ and oligo dT$_{10}$ purified mRNA using Oligo-dT$_{(8+12)}$ primers for mRNA generation and subsequently 1$^{st}$-strand cDNAs synthesized. The pooled mRNA used for 1$^{st}$-strand cDNA synthesis with the help of AMV transcriptase by RT reaction. 1$^{st}$-strand quality was assured by amplifying standard housekeeping genes as control e.g. β-actin gene. PCR amplified 694 bp putative hGH-V fragment (SEQ ID NO: 1) is cloned directly by TA-cloning into pUC-18 based vectors. All the positive clones have undergone through restriction analysis (using AatII, BstXI, NcoI, NotI, PstI) to check the validity of the fragment as well as the orientation of the fragment within the vector. Results confirm the validity of the 694 bp fragment (SEQ ID NO: 1) as hGH-V cDNA.

HGH-N cDNA fragment was also generated using the fetal pituitary mRNA following the same procedure as mentioned above. Four independent RT-PCR amplified putative 723 bp hGH-N fragment (SEQ ID NO: 2) is cloned directly by TA-cloning into pUC-18 based vectors (pGEHN). Using eight unique restriction enzymes from human hGH-N cDNA map the validity of the cloned fragments was checked which showed that the 723 bp RT-PCR product (SEQ ID NO: 2) from fetal pituitary and brain are both putative hGH-N cDNA.

Since hGH-N was analyzed for codon optimization according to *E. coli* codon degeneracy, which shows most of the regions, are similar to the codon usage (Gray et al., 1988; U.S. Pat. No. 4,604,359). In a preferred embodiment only two amino acids in the mature ORF were manipulated in their wobble sequence, which created a unique restriction site Example 4

Analysis by Sequencing

The constructs were sequenced using normal sequencing protocol, which is modified in the laboratory. DNA to be sequenced, either a PCR product or a plasmid construct, was purified through column or through PEG precipitation described in Kraft et al. 1988. After purification, sample DNA has given for sequencing in the range of 50 ng to 500 ng. Cycle sequencing reactions are made up in a final volume of either 10 μl or 20 μl. For each reaction either 4 μl or 8 μl terminator ready reaction mix is added to the DNA template. This ready reaction mix has pre-mixed dNTPs, dye terminator, ampli Taq DNA polymerase, MgCl$_2$ and buffer. Addition of 1 μl of primer (5 pmoles/μl), tubes are subjected to cycle sequencing in a thermal cycler (25 cycles of 94° C., 10 secs, 50° C. for 5 sec and 60° C. for 4 mins).

The PCR product was precipitated with 2.7 M sodium acetate (pH 4.6) and ethanol, washed twice with 70% ethanol and the final DNA pellet was resuspended in formamide. Samples were then analysed in the automated sequence (310 Genetic Analyzer from ABI Technology).

Example 5

Construction of the Chimeric cDNA

In our strategy, the difference in amino acids (13 total) between hGH-V from hGH-N had taken into consideration where the changes are done on hGH-V clone in such a way so that those amino acids are replaced with the hGH-N cDNA stretch, which also consequently made a *E. coli*-able modified hGH cDNA product. We had taken the previously cloned hGH-V and hGH-N cDNA in the pUC-18 based vector. These clones (pGEHV and pGEHN) are digested separately with unique restriction enzymes to replace the hGH-V fragment's specific regions with *E. coli*-able hGH-N portions or synthetic constructs. Then the final hGH-NV chimera was cloned using restriction enzymes the digested fragments are ligated with each other to ligate back into TA-cloning vector in between NcoI/NotI site. Restriction analysis was done to confirm the ligated hGH-NV chimera within the same pUC-18 based TA-cloning vector (Yanisch-Perron et al., 1985).

Cloning of hGH-NV cDNA chimera was done on pUC-18 based cloning vector pGEHNV at NcoI/NotI site (FIG. 5a) as well as into pBAD promoter (or similar promoters) (pBAD/HisA) controlled *E. coli* expression vector and transformed TOP10 *E. coli* strain with that. Ligation reactions were done by incubating the reaction mix overnight at 4° C. for 16 hrs. To increase the number of transformants it was necessary to incubate the ligation reaction mix in this manner. For transformation, regular protocol was followed where after incubation 100 μl-200 μl transformation mix was spreaded onto the 2XYT agar plates with 50 μg/μl of ampicillin present. More than 50-70 colonies were present per plate; control plate was set using linearized vector. DNA extraction was done by following miniprep DNA extraction with the help of alkaline-lysis procedure as mentioned above. A thorough restriction analysis was done after a putative positive clone was achieved with NcoI/Eco24I, NheI/EheI, NcoI/XhoI, BshTI/XhoI/BstXI, BshTI/XhoI, NcoI/EcoRI were used to check the insert restriction map.

To check the hGH-NV expression in *E. coli* we were trying to clone the chimeric cDNA into pBAD/HisA expression vector. Applicants are interested in cloning of only the portion of cDNA, which represent the mature peptide region excluding the 26 amino acids, the secretory signal peptide. To achieve that gene-specific primer pairs are made at the start (Primer E, SEQ ID NO: 12) and stop (Primer F, SEQ ID NO: 13) of mature peptide region. At the same time to clone the mature hGH-NV immediately after factor VIIIa and/or EK cleavage site within the vectors primer pairs (Primers Q & R; SEQ ID NOs:17 and 18) of the vector fragment are designed in such a way so that the mature hGH-NV cDNA gets locked in with the vector fragment portion by T-A cloning method.

Using this unique strategy applicant has achieved 7 positive clones of hGH-NV in pBAD/HisA expression vectors (or similar vectors).

An extensive restriction analysis on two of the six mature chimeric clones from TOP10 *E. coli* expressible strain (or similar strains) and confirmed that these clones are the putative hGH-NV mature cDNA clones which are ligated in the right orientation on the vector by T-A ligation. It's to be noted that hGH-NV (SEQ ID NO: 3) sequence differs from hGH-N sequence in codon usage, one additional restriction site and mRNA secondary structure (FIGS. 3 & 4) and the synthetic hGH-NV gives identical protein sequence as that of somatotropin (FIG. 2).

Example 6

Making of the Multiple Cassettes

Unique strategy was taken to insert the multiple cassettes of the coding domain including the regulatory region in tandem fashion. This helped to increase the level of recombinant hGH-NV derived human growth hormone expression in *E. coli* which is distinctly showing the promising difference in its expression level (FIG. 8). Here, cloning of the multicassettes into arabinose-inducible (or similar induction systems) expression vector (pABGH2) as total of 7275 bp.

In this attempt, our interest lies in cloning of hGH mature cDNA in the form of duplicate cassettes in inducible expression vector for high-level expression in *E. coli*. A thorough analysis was done on expressed protein that showed the right mol. wt. protein band on SDS-PAGE, and further confirmed by Western blotting, N-terminal amino acid sequencing and protease cleavage mapping (unpublished data). Since the previous clone showed only 5% of total *E. coli* protein expression, we have focused in modifying hGH Clone #1 (pABGH1,). We have achieved at least eight of such positive clones by applying a strategy of ligation and cloning. This unique clone consists of multiple copies of promoter-hGH insert-terminator cassette. Confirmation of positive clones was done by several combination of restriction enzyme analysis. Analysis by quick induction experiment followed by SDS-PAGE reveals the level of expression gone up to higher than the previous hGH Clone #1 (pABGH1) To achieve even for better level of expression induction was done in an optimized media with various inducers.

A thorough restriction analysis was done on the positive clones. PvuI digestion on the miniprep DNA was taken as our screening method for selecting positives.

Maxiprep DNA from hGH clone #1 (pABGH1) were digested with AccI/BshTI, BshTI/EcoRI and AccI/EcoRI to get 1965 bp, 1282 bp, 903 bp, 3717 bp and 470 bp DNA fragments, respectively. After 2 hrs of digestion at 37° C. digested samples were run on 1.2% agarose gel and the above mentioned bands were purified for ligation.

Restriction enzyme digested (pABGH1) maxiprep DNA is showing the gel-purified fragment of interest. pABGH1 clone double digested with AccI/BshTI, showing 1965 bp and 1282 bp DNA fragments of interest pABGH1 double digested with BshTII/EcoRI, showing purified 903 bp digested fragment pABGH1 clone double digested with AccI/EcoRI. 470 bp and 1965 bp purified bands of interest those will be ligated.

These three DNA fragments are ligated one after another, which contain the regulatory, hGH cDNA insert and the 3'-downstream terminator regions. This whole 2655 bp cassette is finally circularized by ligated with the 1965 bp fragment. Total length of the plasmid construct comes to 7275 bp (SEQ ID NO: 18, FIG. 5b) where the insert size is 2655 bp which is inserted as duplicated cassettes arranged in tandem.

All the SEQ ID NOs: are tabulated accordingly in Table 3.

Production at Lab Scale

Intention of cloning multiple cassettes of hGH-NV into the arabinose-inducible expression vector was to increase the expression level for production at later stage. This intention was successful at least 1 L scale, yielding 4-5 g/L hGH (or higher) was produced in an appropriate fermentation condition. Comparative protein expression level in single synthetic hGH, duplicated cassettes were given in FIG. 8.

Some Advantages of Present Invention:
1. Novel chimera produced from two isoforms viz., hGH-V and hGH-N for better codon usage in prokaryotic cells.
2. hGH-NV cDNA chimera is obtained without the use of site-directed mutagenesis.
3. Better expression of hGH because of modified codon usage without the use of helper vector and without compromising the protein sequence.
4. Enhanced level of expression of the hGH is possible due to duplication of the expressible construct derived from hGH-NV cDNA chimera along with its regulatory elements from the vector.

TABLE 1

(Taken from Ausubel, F. M. et al., 1987)

| AA | Codon | Mammal freq. | % | Other freq. | Vertebrate % | Yeast freq. | % | Gram freq. | neg. % | G. freq | pos. % |
|---|---|---|---|---|---|---|---|---|---|---|---|
| Gly | GGG | 16.6 | 22.8 | 14.8 | 20.7 | 5.2 | 9.0 | 9.4 | 12.3 | 9.2 | 13.7 |
| Gly | GGA | 18.5 | 25.5 | 20.9 | 29.2 | 8.5 | 15.0 | 7.0 | 9.2 | 20.5 | 30.5 |
| Gly | GGU | 12.8 | 17.6 | 15.2 | 21.3 | 34.9 | 61.0 | 25.1 | 32.9 | 18.2 | 27.2 |
| Gly | GGC | 24.7 | 34.1 | 20.7 | 28.9 | 8.9 | 15.0 | 34.9 | 45.6 | 19.1 | 28.5 |
| Pro | CCG | 6.8 | 11.2 | 6.0 | 11.0 | 4.1 | 9.0 | 23.7 | 54.4 | 10.8 | 30.3 |
| Pro | CCA | 16.5 | 27.3 | 16.7 | 30.4 | 21.9 | 49.0 | 7.4 | 17.1 | 10.3 | 28.9 |
| Pro | CCU | 17.4 | 28.8 | 15.7 | 28.6 | 12.7 | 29.0 | 6.6 | 15.2 | 11.9 | 33.2 |
| Pro | CCC | 19.7 | 32.7 | 16.4 | 30.0 | 5.7 | 13.0 | 5.8 | 13.3 | 2.7 | 7.6 |
| Stop | UAA | 1.0 | 23.2 | 1.4 | 28.0 | 1.0 | 49.0 | 1.8 | 57.2 | 2.1 | 65.6 |
| Stop | UAG | 0.7 | 17.2 | 0.7 | 13.8 | 0.4 | 17.0 | 0.3 | 9.7 | 0.5 | 15.6 |
| Stop | UGA | 2.6 | 59.6 | 2.9 | 58.1 | 0.7 | 34.0 | 1.0 | 33.2 | 0.6 | 18.9 |
| Phe | UUU | 15.3 | 40.7 | 14.6 | 44.2 | 22.7 | 53.0 | 17.1 | 47.5 | 27.3 | 68.0 |
| Phe | UUC | 22.3 | 59.3 | 18.4 | 55.8 | 20.0 | 47.0 | 18.9 | 52.5 | 12.8 | 32.0 |

TABLE 2

| | 24 Hours | 48 Hours | 72 hours |
|---|---|---|---|
| Control | $1.25 \times 10^5$ +/− 0.11 | $1.72 \times 10^5$ +/− 0.27 | $2.05 \times 10^5$ +/− 0.11 |
| 0.1 ng Novo Nordisk | $1.72 \times 10^5$ +/− 0.18 | $5.07 \times 10^5$ +/− 0.55 | $5.30 \times 10^5$ +/− 0.92 |
| 1 ng Novo Nordisk | $1.73 \times 10^5$ +/− 0.06 | $6.50 \times 10^5$ +/− 0.45 | $10.12 \times 10^5$ +/− 0.27 |
| 10 ng Novo Nordisk | $1.79 \times 10^5$ +/− 0.27 | $8.37 \times 10^5$ +/− 0.73 | $16.35 \times 10^5$ +/− 1.15 |
| 0.1 ng GH produced as per novel process of the present invention | $1.49 \times 10^5$ +/− 0.11 | $2.53 \times 10^5$ +/− 0.29 | $5.20 \times 10^5$ +/− 0.66 |
| 1 ng GH produced as per novel process of the present invention | $2.04 \times 10^5$ +/− 0.22 | $5.90 \times 10^5$ +/− 0.42 | $11.8 \times 10^5$ +/− 0.74 |
| 10 ng GH produced as per novel process of the present invention | $1.95 \times 10^5$ +/− 0.22 | $9.1 \times 10^5$ +/− 0.44 | $19.05 \times 10^5$ +/− 1.73 |

We claim:

1. A hGH-NV cDNA chimera having the sequence as shown in SEQ ID NO:3, from residue number 1 to 728.

2. A plasmid vector comprising the hGH-NV cDNA chimera of claim 1.

3. The plasmid vector of claim 2, wherein said plasmid vector comprises the plasmid vector pABGH2.

4. A process for the production of human growth hormone, comprising the steps of:
   a) transforming a host with the plasmid vector of claim 3;
   b) culturing said host under suitable conditions to express human growth hormone; and
   c) recovering said human growth hormone.

5. The plasmid vector of claim 2, wherein said plasmid vector is suitable for transformation in *E. coli*.

6. A process for the production of human growth hormone, comprising the steps of:
   a) transforming a host with the plasmid vector of claim 5;
   b) culturing said host under suitable conditions to express human growth hormone; and
   c) recovering said human growth hormone.

7. A process for the production of human growth hormone, comprising the steps of:
   a) transforming a host with the plasmid vector of claim 2;
   b) culturing said host under suitable conditions to express human growth hormone; and
   c) recovering said human growth hormone.

8. A process for the production of human growth hormone, comprising the steps of:
   a) transforming a host with the cDNA of claim 1;
   b) expressing the protein encoded by said cDNA to make human growth hormone; and
   c) recovering said human growth hormone.

* * * * *